United States Patent
Jacobsen et al.

(10) Patent No.: US 9,309,165 B2
(45) Date of Patent: Apr. 12, 2016

(54) 6-CHLORO-3-(PHENYL-D5)-INDEN-1-ONE AND USE THEREOF

(71) Applicant: H. Lundbeck A/S, Valby (DK)

(72) Inventors: Mikkel Fog Jacobsen, Frederiksberg (DK); Sebastian Brandes, Roskilde (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 14/653,318

(22) PCT Filed: Dec. 19, 2013

(86) PCT No.: PCT/EP2013/077314
§ 371 (c)(1),
(2) Date: Jun. 18, 2015

(87) PCT Pub. No.: WO2014/096151
PCT Pub. Date: Jun. 26, 2014

(65) Prior Publication Data
US 2015/0336867 A1 Nov. 26, 2015

Related U.S. Application Data

(60) Provisional application No. 61/739,095, filed on Dec. 19, 2012.

(30) Foreign Application Priority Data

Dec. 19, 2012 (DK) .................................. 2012 00811

(51) Int. Cl.
*C07C 49/00* (2006.01)
*C07D 295/00* (2006.01)
*C07D 209/00* (2006.01)
*C07B 59/00* (2006.01)
*C07C 49/697* (2006.01)
*C07D 295/073* (2006.01)

(52) U.S. Cl.
CPC .............. *C07B 59/001* (2013.01); *C07C 49/697* (2013.01); *C07B 2200/05* (2013.01); *C07D 295/073* (2013.01)

(58) Field of Classification Search
CPC C07C 49/697; C07B 59/001; C07B 2200/05; C07D 295/023
USPC ........................... 568/316, 327; 544/404, 405
See application file for complete search history.

(56) References Cited

FOREIGN PATENT DOCUMENTS

| EP | 2639216 | 9/2013 |
|----|---------|--------|
| WO | 2005/016900 A1 | 2/2005 |
| WO | 2005/016901 A1 | 2/2005 |
| WO | 2006/086984 A1 | 8/2006 |
| WO | 2012/176066 A1 | 12/2012 |

OTHER PUBLICATIONS

William M. Clark et al., 1999, "A Highly Enantioselective Conjugate Reduction of 3-arylinden-1-ones Using Bakers' Yeast for the Preparation of (s)-3-Arylindan-1-ones", Organic Letters, American Chemical Society, vol. 1, No. 11, pp. 1839-1842, XP002951487.

*Primary Examiner* — Sikarl Witherspoon
(74) *Attorney, Agent, or Firm* — Mary Catherine Di Nunzio; Jeffrey I. Auerbach

(57) ABSTRACT

The present invention discloses the compound 6-chloro-3-(phenyl-$d_5$)-inden-1-one (I) and routes of synthesis to obtain (I). In a further aspect the present invention discloses the use of (I) for the synthesis of (S)-6-chloro-3-(phenyl-$d_5$)-indan-1-one.

16 Claims, No Drawings

6-CHLORO-3-(PHENYL-D5)-INDEN-1-ONE AND USE THEREOF

CROSS-REFERENCE TO RELATED APPLICATIONS

The present application is a §371 U.S. National Stage Application of PCT International Application No. PCT/EP2013/077314, filed Dec. 19, 2013, which claims benefit of priority under 35 U.S.C. §119(e) of U.S. Provisional Application No. 61/739,095, filed Dec. 19, 2012 and which claims the benefit of priority under 35 U.S.C. §119(a)-(d) of Danish Application No. PA201200811, filed Dec. 19, 2012. Each of these applications is hereby incorporated by reference in its entirety.

FIELD OF THE INVENTION

The present invention relates to 6-chloro-3-(phenyl-$d_5$)-inden-1-one, use of the compound as well as processes for preparation of the compound.

BACKGROUND OF THE INVENTION

Deuterated 1-piperazino-3-phenyl-indanes for treatment of schizophrenia have been disclosed in U.S. application Ser. No. 13/527,364. U.S. application Ser. No. 13/527,364 also discloses how specific deuterated 1-piperazino-3-phenyl-indanes can be obtained via 6-chloro-3-(phenyl-$d_5$)-indan-1-one. However, the disclosed routes for synthesis of both racemic and enantiomerically pure 6-chloro-3-(phenyl-$d_5$)-indan-1-one rely on the uneconomical use of high loading of either a chiral rhodium catalyst or a chiral palladium catalyst. Accordingly, new processes for the synthesis of racemic and enantiomerically pure 6-chloro-3-(phenyl-$d_5$)-indan-1-one are desirable, and are herein described proceeding via the compound 6-chloro-3-(phenyl-$d_5$)-inden-1-one (I).

Clark, W. M. et al in *Organic Letter*, 1999, Vol. 1, No. 11, pp. 1839-1842 attempted the preparation of 3-arylindenones, such as 6-chloro-3-(phenyl-$d_5$)-indan-1-one (I), with electron-withdrawing groups (Cl, Br, $NO_2$) at the C(5)- or C(6)-position of the indenone ring using a Suzuki methodology, but failed to obtain appreciable amounts of the desired products. In contrast, the present invention describes the successful preparation of such 3-arylindenones, e.g. 6-chloro-3-(phenyl-$d_5$)-indan-1-one (I), via a Suzuki methodology.

SUMMARY OF THE INVENTION

The present invention discloses the compound 6-chloro-3-(phenyl-$d_5$)-inden-1-one (I)

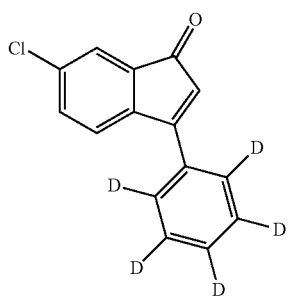

I and routes of synthesis to obtain (I). In a further aspect the present invention discloses the use of 6-chloro-3-(phenyl-$d_5$)-inden-1-one (I) to obtain racemic 6-chloro-3-(phenyl-$d_5$)-indan-1-one (VIII) or (S)-6-chloro-3-(phenyl-$d_5$)-indan-1-one (IX).

Further the present invention discloses use of 6-chloro-3-(phenyl-$d_5$)-inden-1-one (I) to obtain 4-((1R,3S)-6-chloro-3-(phenyl-$d_5$)-indan-1-yl)-1($d_3$),2,2-trimethyl-piperazine and pharmaceutically acceptable salts thereof.

DETAILED DESCRIPTION OF THE INVENTION

Compound List (I): 6-chloro-3-(phenyl-$d_5$)-inden-1-one (II): 6-chloro-1-indanone (III): 3-bromo-6-chloro-inden-1-one (IV): 6-chloro-3-(phenyl-$d_5$)-1H-indene (V): 5-chloro-1-indanone (VI): (±)-6-chloro-3-(phenyl-$d_5$)-1H-inden-1-ol (VIa) 6-chloro-3-(phenyl-$d_5$)-1H-inden-1-ol (VII): (S)-6-chloro-3-(phenyl-$d_5$)-1H-inden-1-ol (VIII): (±)-6-chloro-3-(phenyl-$d_5$)-indan-1-one (VIIIa): 6-chloro-3-(phenyl-$d_5$)-indan-1-one (IX): (S)-6-chloro-3-(phenyl-$d_5$)-indan-1-one (X): (±)-cis-6-chloro-3-(phenyl-$d_5$)-indan-1-ol (Xa): (1S,3S)-6-chloro-3-(phenyl-$d_5$)-indan-1-ol (Xb): 6-chloro-3-(phenyl-$d_5$)-indan-1-ol (XI): (±)-cis-3,5-dichloro-1-(phenyl-$d_5$)-indan (XIa): (1S,3S)-3,5-dichloro-1-(phenyl-$d_5$)-indan (XIb): 3,5-dichloro-1-(phenyl-$d_5$)-indan (XII): (±)-trans-1-(6-chloro-3-(phenyl-$d_5$)-indan-1-yl)-3,3-dimethyl-piperazine maleate (XIIa): 1-((1R,3S)-6-chloro-3-(phenyl-$d_5$)-indan-1-yl)-3,3-dimethyl-piperazine maleate (XIIb): Pharmaceutically acceptable salt of 1-(6-chloro-3-(phenyl-$d_5$)-indan-1-yl)-3,3-dimethyl-piperazine (XIII): (±)-trans-4-(6-chloro-3-(phenyl-$d_5$)-indan-1-yl)-1($d_3$),2,2-trimethyl-piperazine succinate (XIIIa): 4-(6-chloro-3-(phenyl-$d_5$)-indan-1-yl)-1($d_3$),2,2-trimethyl-piperazine (XIV): 4-((1R,3S)-6-chloro-3-(phenyl-$d_5$)-indan-1-yl)-1($d_3$),2,2-trimethyl-piperazine L-(+)-tartrate (XV): 4-((1R,3S)-6-chloro-3-(phenyl-$d_5$)-indan-1-yl)-1($d_3$),2,2-trimethyl-piperazine fumarate (XVa) Pharmaceutically acceptable salt of 4-((1R,3S)-6-chloro-3-(phenyl-$d_5$)-indan-1-yl)-1($d_3$),2,2-trimethyl-piperazine (XVI): 1($d_3$),2,2-trimethylpiperazine Bis-2,2,2-trifluoroacetate (XVII): 2,2-dimethylpiperazine (XVIII): tert-butyl 3,3-dimethylpiperazine-1-carboxylate hemi-D,L-tartrate (XIX): (E)-1-(6-chloro-3-phenyl($d_5$)-1H-inden-1-ylidenemethyl)-N,N-dimethylamine The present invention provides the compound (I)

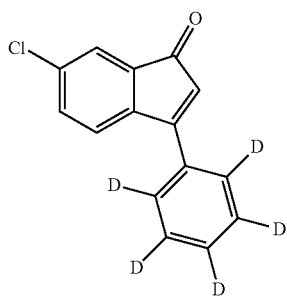

I and synthetic routes for preparation of the compound as well as the use of the compound for the preparation of 4-((1R,3S)-6-chloro-3-(phenyl-$d_5$)-indan-1-yl)-1($d_3$),2,2-trimethyl-piperazine and pharmaceutically acceptable salts of 4-((1R,3S)-6-chloro-3-(phenyl-$d_5$)-indan-1-yl)-1($d_3$),2,2-trimethyl-piperazine.

The present invention discloses how synthesis of compound (I) can be accomplished by a first step comprising the synthesis of compound (III) followed by a second step where (III) is reacted with an arylboronic acid or ester, e.g. 4,4,5,5-tetramethyl-2-$d_5$-phenyl-[1,3,2]dioxaborolane, in the presence of an appropriate catalyst, e.g. palladium(II) acetate, and base, e.g. potassium phosphate.

The present invention further discloses how the synthesis of compound (I) can be accomplished from compound (IV) via oxidation of an enamine (XIX), e.g. in the presence of a periodate-salt.

In a further aspect the present invention discloses the use of compound (I) for the preparation of compound (VIII) or (IX) by either of the following pathways.
(1) Reduction followed by rearrangement to obtain compound (VIII) (pathways B and D2 in Scheme 1, below)
(2) Enantioselective reduction followed by rearrangement to obtain compound (IX) (pathways C and E1 in Scheme 1, below)
(3) Hydrogenation to obtain compound (VIII) (pathway D1 in Scheme 1, below)
(4) Organocatalytic asymmetric transfer hydrogenation to obtain compound (IX) (pathway E2 in Scheme 1, below)
(5) Asymmetric hydrogenation to obtain compound (IX) (pathway E3 in Scheme 1, below).

These synthetic pathways of the invention can be summarized as follows:

Scheme 1: Preparation of compounds (I), (VI)/(VIa), (VII), (VIII)/(VIIIa) and (IX)

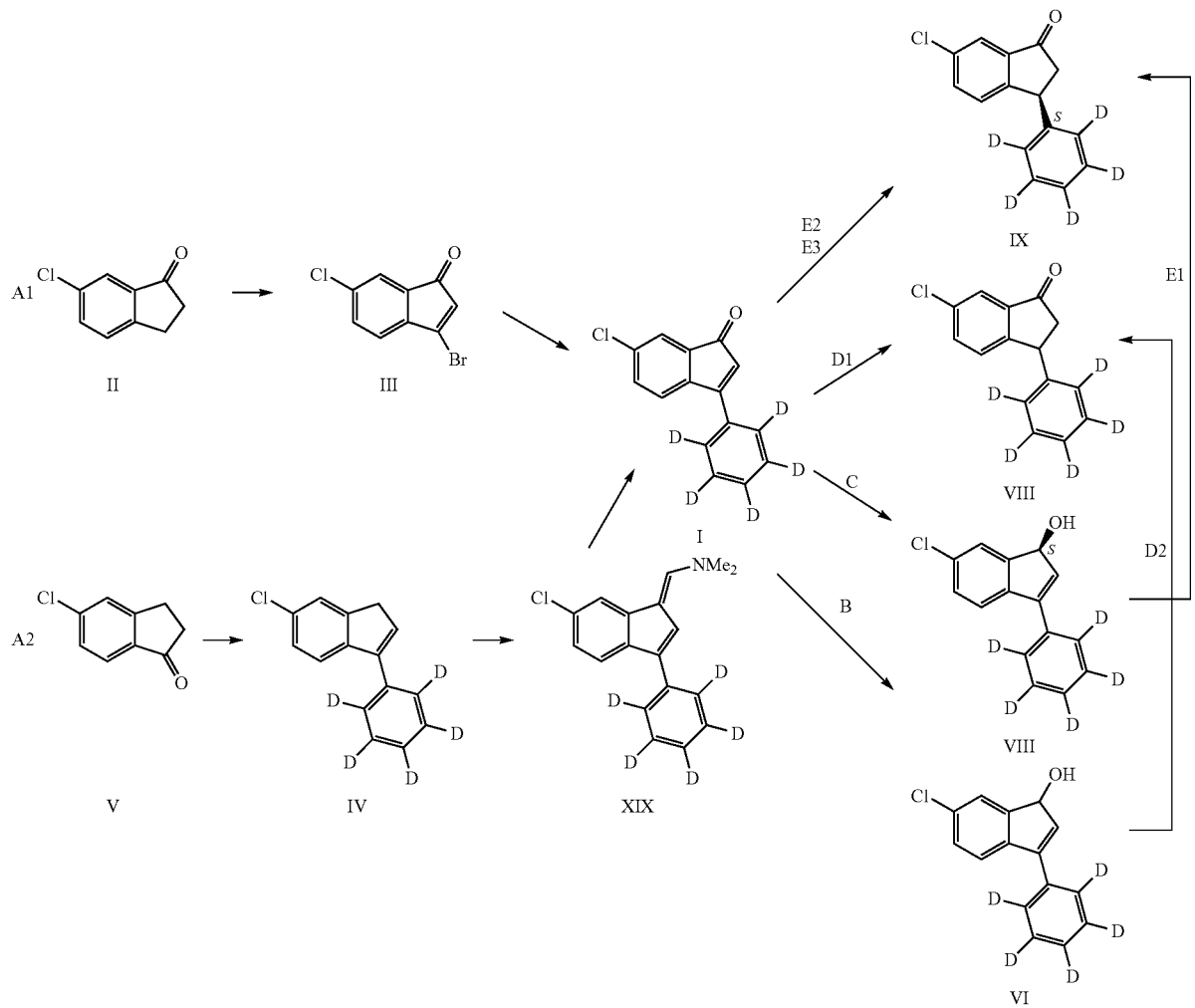

In a further aspect the present invention discloses the use of compound (VIII) obtained as disclosed above for the preparation of compound (XIV) via compounds (X), (XI), (XII) and (XIII) (pathway A and B in Scheme 2).

In a further aspect the present invention discloses the use of compound (IX) obtained as disclosed above for the preparation of compound (XV) or compound (XIV) via compounds (Xa) and (XIa) (pathway C in Scheme 2).

In a further aspect the present invention discloses the use of compound (IX) obtained as disclosed above for the preparation of compound (XV) or compound (XIV) via compounds (Xa), (XIa) and (XIIa) (pathway A and B in Scheme 2).

In another aspect the present invention discloses the preparation of compound (XVI) from compound (XVII) via compound (XVIII) (Scheme 2).

The synthetic pathways of the invention can be summarized as follows:

The invention will be illustrated in the following non-limiting examples.

Embodiments According to the Invention

Unless otherwise specified the reference to any of the compounds in the embodiments below covers the enantiomerically pure compound or mixtures of the enantiomers in any ratio. For example compound (VIIIa) 6-chloro-3-(phenyl-$d_5$)-indan-1-one refers to the racemic mixture of (VIIIa), i.e. (±)-6-chloro-3-(phenyl-$d_5$)-indan-1-one, as well as the enantiomers of (VIIIa) in any ratio.

In a first embodiment (E1) the present invention relates to the compound having the structure (I) (also referred to as compound of formula (I) or compound (I))

Scheme 2: Preparation of compounds (XIII), (XIV), (XV) and (XVI)

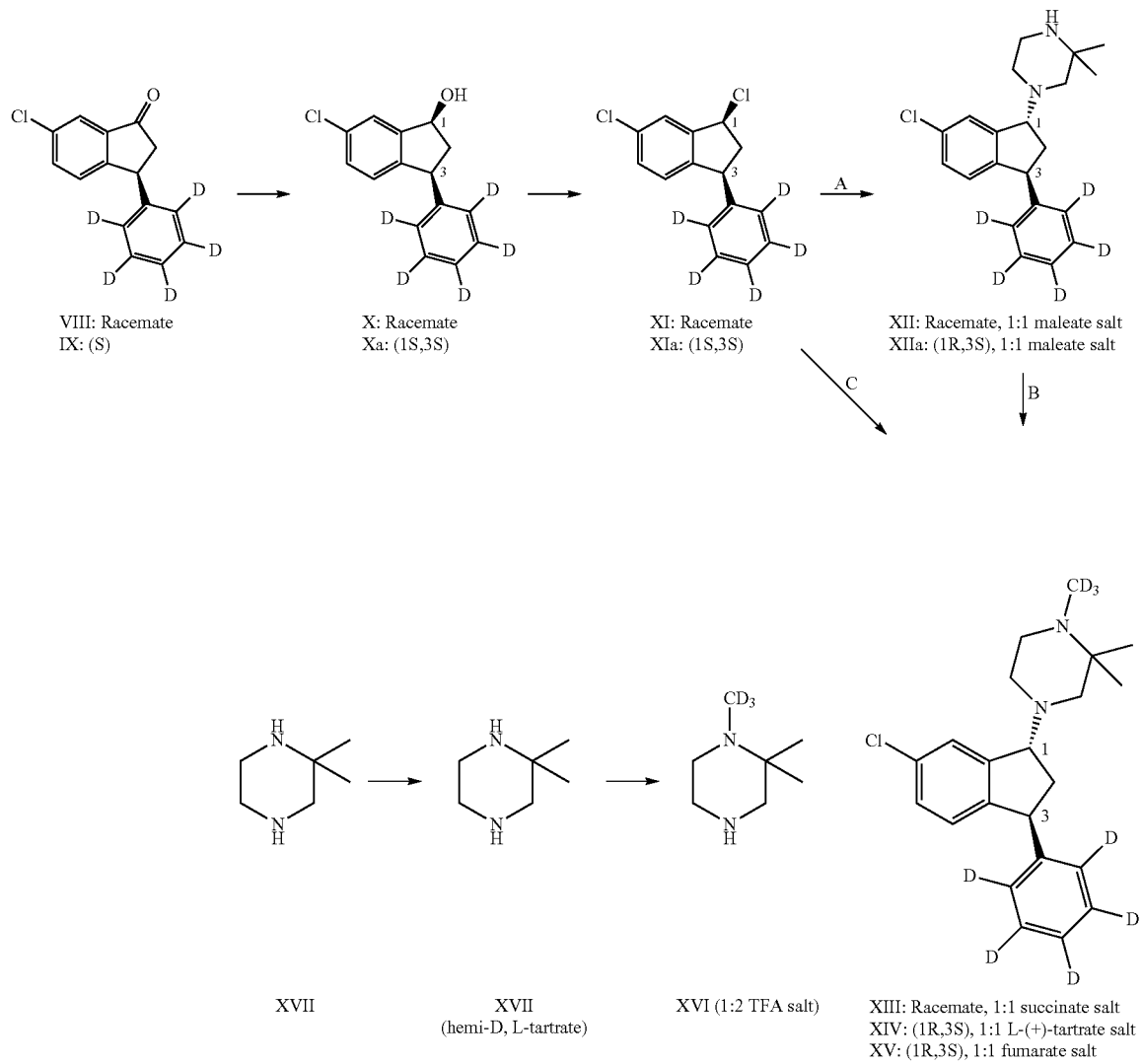

In an (E2) compound (I) of (E1) is obtained from the reaction of 3-bromo-6-chloro-inden-1-one (III) with boronic acid or ester of phenyl-$d_5$.

In a further embodiment (E3) of (E2) compound (III) is obtained from (II) as a starting material.

In a further embodiment (E4) of (E3) the synthesis of compound (I) comprises the following steps:
1. Bromination of compound (II), e.g. by addition of 2,2'-azo-bis-isobutyronitrile and N-bromosuccinimide to a solution comprising 6-chloro-1-indanone (II).
2. Base-induced elimination by addition of a base, e.g. triethylamine, to the solution of step 1 to obtain 3-bromo-6-chloro-inden-1-one (III).
3. 3-bromo-6-chloro-inden-1-one (III) obtained in step 2 is optionally separated and reacted with a phenyl-$d_5$ boronic acid or ester, e.g. 4,4,5,5-tetramethyl-2-$d_5$-phenyl-[1,3,2]dioxaborolan, in the presence of an appropriate catalyst and base to obtain compound (I).

In an embodiment (E5) of (E1)) the synthesis of compound (I) comprises the following steps:
1. Synthesis of 6-chloro-3-(phenyl-$d_5$)-1H-indene (IV) by reaction between an organometallic species (obtained from monohalogenated benzene-$d_5$) and 5-chloro-1-indanone (V) followed by dehydration.
2. Reaction of 6-chloro-3-(phenyl-$d_5$)-1H-indene (IV) to compound (XIX) and further oxidative cleavage thereof to obtain compound (I).

In an embodiment (E6) of (E5) compound (I) is obtained by a process comprising:
1. Synthesis of 6-chloro-3-(phenyl-$d_5$)-1H-indene (IV) by Grignard reaction between bromobenzene-$d_5$, magnesium and 5-chloro-1-indanone (V) followed by dehydration.
2. Reacting 6-chloro-3-(phenyl-$d_5$)-1H-indene (IV) with 1,1-dimethoxy-N,N-dimethylmethanamine followed by oxidative cleavage of the formed compound (XIX) to obtain compound (I).

In a further embodiment (E7) of (E5) and (E6) the oxidative cleavage in the synthesis of compound (I) is carried out by use of an oxidative agent selected from the group consisting of sodium metaperiodate, potassium metaperiodate, ozone, potassium dichromate, sodium dichromate, singlet oxygen and m-chloroperbenzoic acid.

In a particular embodiment (E8) of (E7) the oxidative cleavage is carried out by use of sodium metaperiodate.

In an embodiment (E9) compound (I) of (E1) is reduced to obtain (VIa), in particular (±)-6-chloro-3-(phenyl-$d_5$)-1H-inden-1-ol (VI).

In a further embodiment (E10) of (E9) the reduction takes place in the presence of reductants selected from the group consisting of sodium borohydride, magnesium borohydride, calcium borohydride, lithium borohydride, sodium triacetoxyborohydride, lithium triacetoxyborohydride, lithium aluminium hydride, sodium bis(2-methoxyethoxy)aluminum dihydride, diisobutylaluminium hydride and lithium triethylborohydride.

In a particular embodiment (E11) of (E10) the reduction takes place in the presence of diisobutylaluminium hydride.

In an embodiment (E12) compound (VIa) of (E9) is converted to (VIIIa), in particular (±)-6-chloro-3-(phenyl-$d_5$)-indan-1-one (VIII), via base-induced rearrangement.

In an embodiment (E13) compound (I) of (E1) is converted to (S)-6-chloro-3-(phenyl-$d_5$)-1H-inden-1-ol (VII) via enantioselective reduction.

In a particular embodiment (E14) of (E13) the enantioselective reduction takes place in the presence of enantioselective catalysts and reductants selected from the group consisting of enantiomerically pure 2-methyl-CBS-oxazaborolidine, o-tolyl-CBS-oxazaborolidine, 2-Butyl-CBS-oxazaborolidine, Alpine-Borane® and B-chlorodiisopinocampheylborane.

In a particular embodiment (E15) of (E14) the enantioselective reduction takes place in the presence of enantiomerically pure 2-Methyl-CBS-oxazaborolidine.

In an embodiment (E16) of (E13) to (E15) compound (VII) is converted to (S)-6-chloro-3-(phenyl-$d_5$)-indan-1-one (IX) via base-induced rearrangement.

In a further embodiment (E17) of any of (E12) and (E16) the base-induced rearrangement takes place in the presence of a suitable base selected from the group consisting of 1,4-diazabicyclo[2.2.2]octane, potassium bis(trimethylsilyl)amide and lithium bis(trimethylsilyl)amide.

In a particular embodiment (E18) of (E17) the base-induced rearrangement takes place in the presence of 1,4-diazabicyclo[2.2.2]octane.

In an embodiment (E19) compound (I) of (E1) is converted to obtain (VIIIa), in particular (±)-6-chloro-3-(phenyl-$d_5$)-indan-1-one (VIII) via hydrogenation in the presence of a suitable catalyst in a suitable solvent.

In a specific embodiment (E20) of (E19) compound (I) is converted to compound (VIII) in the presence of tris(triphenylphosphine)rhodium(I) chloride.

In a specific embodiment (E21) of (E19) the solvent is ethyl acetate.

In an embodiment (E22) compound (I) of (E1) is converted to (S)-6-chloro-3-(phenyl-$d_5$)-indan-1-one (IX) via asymmetric hydrogenation in the presence of a suitable catalyst in a suitable solvent.

In a further embodiment (E23) of (E22) the asymmetric hydrogenation of compound (I) is carried out in the presence of a rhodium-salt.

In a further embodiment (E24) of any of (E22) and (E23) the asymmetric hydrogenation of (I) is carried out in the presence of a chiral phosphine ligand.

In a specific embodiment (E25) of (E23) the rhodium-salt selected is from the group consisting of bis(norbornadiene)rhodium(I) trifluoromethanesulfonate, bis(norbornadiene)rhodium(I) tetrafluoroborate, bis(1,5-cyclooctadiene)rhodium(I) trifluoromethanesulfonate, bis(norbornadiene)rhodium(I) tetrafluoroborate and bis(1,5-cyclooctadiene)rhodium(I) tetrakis[(bis(3,5-trifluoromethyl)phenyl]borate.

In a specific embodiment (E26) of (E24) the chiral phosphine ligand selected from the group consisting of (R)-(−)-5,5'-bis[di(3,5-di-tert-butyl-4-methoxyphenyl)phosphino]-4,4'-bi-1,3-benzodioxole ((R)-DTBM-SEGPHOS), (S)-(+)-4,12-bis(diphenylphosphino)-[2.2]-paracyclophane ((S)-Phanephos) and (S)-(+)-4,12-bis[di(3,5-xylyl)phosphino]-[2.2]-paracyclophane ((S)-DM-Phanephos).

In a specific embodiment (E27) of (E22) the solvent is ethyl acetate.

In an embodiment (E28) compound (VIII) of any of embodiments (E12) and (E19) is converted to (Xb), in particular (±)-cis-6-chloro-3-(phenyl-$d_5$)-indan-1-ol (X).

In an embodiment (E29) of any of embodiments (E16) to (E18) and (E22) to (E27) (S)-6-chloro-3-(phenyl-$d_5$)-indan-1-one (IX) is converted to (1S,3S)-cis-6-chloro-3-(phenyl-$d_5$)-indan-1-ol (Xa).

In an embodiment (E30) of (E28) (Xb) is converted to (XIb) by chlorination, in particular (±)-cis-6-chloro-3-(phenyl-$d_5$)-indan-1-ol (X) is converted to (±)-cis-3,5-dichloro-1-(phenyl-$d_5$)-indan (XI) by chlorination.

In an embodiment (E31) of (E29) (1S,3S)-6-chloro-3-(phenyl-$d_5$)-indan-1-ol (Xa) is converted to (1S,3S)-3,5-dichloro-1-(phenyl-$d_5$)-indan (XIa) by chlorination.

In a further embodiment (E32) of any of (E30) and (E31) the chlorination takes place in the presence of a reagent selected from the group consisting of thionyl chloride, phosphorus oxychloride and phosphorus pentachloride.

In a particular embodiment (E33) of (E32) the chlorination takes place in the presence of thionyl chloride.

In an embodiment (E34) of (E30) 3,5-Dichloro-1-(phenyl-$d_5$)-indan (XIb) is converted to (XIIb) by nucleophilic substitution with 2,2-dimethylpiperazine or a compound that subsequently can be transformed to the 3,3-dimethylpiperazine moiety of (XIIb); in particular (XI) is converted to (XII) by nucleophilic substitution with 2,2-dimethylpiperazine or a compound that subsequently can be transformed to the 3,3-dimethylpiperazine moiety of (XII). In an embodiment (E35) of (E31) (1S,3S)-3,5-Dichloro-1-(phenyl-$d_5$)-indan (XIa) is converted to compound (XIIa) by nucleophilic substitution with 2,2-dimethylpiperazine or a compound that subsequently can be transformed to the 3,3-dimethylpiperazine moiety of compound (XIIa). In a further embodiment (E36) of any of (E34) and (E35) the nucleophilic substitution is carried out with 2,2-dimethylpiperazine in the presence of a base.

In a particular embodiment (E37) of (E36) the base is a carbonate, e.g. potassium carbonate.

In an embodiment (E38) compound (XII) is converted to compound (XIII) by alkylation.

In an embodiment (E39) compound (XIIa) is converted to compound (XVa), such as (XIV) or (XV) by alkylation.

In a further embodiment (E40) of any of (E38) and (E39) the alkylation is carried out in the presence of an active methyl-$d_3$ donor and a base.

In a specific embodiment (E41) of (E40) the active methyl donor is chosen from the group consisting of methyl iodide-$d_3$, methyl bromide-$d_3$ and dimethyl sulfate-$d_6$.

In a particular embodiment (E42) of any of (E40) and (E41) the active methyl donor is methyliodide-$d_3$.

In a specific embodiment (E43) of (E40) the base is chosen from the group consisting of sodium and potassium hydroxide, sodium and potassium carbonate, and sodium and potassium tert-butoxide.

In a particular embodiment (E44) of any of (E40) and (E43) the base is potassium hydroxide. In an embodiment (E45) (1S,3S)-3,5-Dichloro-1-(phenyl-$d_5$)-indan (XIa) of (E31) is converted to compound (XIV) or (XV) by nucleophilic substitution with compound (XVI) or a compound that subsequently can be transformed to the 1($d_3$),2,2-trimethylpiperazine moiety of compound (XIV) or compound (XV).

In a further embodiment (E46) of (E45) the nucleophilic substitution is carried out with compound (XVI) in the presence of a base.

In a specific embodiment (E47) of (E46) the base is chosen from the group consisting of sodium and potassium hydroxide, sodium and potassium carbonate, and sodium and potassium tert-butoxide.

In a particular embodiment (E48) of (E47) the base is potassium carbonate.

In a particular embodiment (E49) of (E46) compound (XVI) is obtained from compound (XVII) via compound (XVIII).

In an embodiment (E50) of any of the previous embodiments the reactions are carried out with compounds comprising hydrogen (H) instead of deuterium (D) thus providing the corresponding non-deuterated compounds.

In an embodiment (E51) of any of the embodiments (E34), (E35), (E38), (E39), (E45) and (E50) the reactions may be carried out to obtain any other pharmaceutically acceptable salt of the compounds (XII), (XIIa), (XIII), (XIV) and (XV).

DEFINITIONS

Enantiomeric excess is defined as the absolute difference between the mole fraction of each enantiomer.

Percent enantiomeric excess is calculated as $$((R-S)/(R+S))*100\%$$

wherein R and S are the respective mole fractions of enantiomers in the mixture such that R+S=1.

The invention will be illustrated in the following non-limiting examples.

The compounds described herein are intended to designate any form of the compound, such as the free base, pharmaceutically acceptable salts thereof, e.g. pharmaceutically acceptable acid addition salts, such as succinate salt, tartrate salt, in particular L-(+)-tartrate salt, and malonate salts, hydrates or solvates of the free base or salts thereof, as well as anhydrous forms, amorphous forms, crystalline forms and solutions.

Pharmaceutically acceptable salts of compounds of the present invention include pharmaceutically acceptable acid addition salts. Acid addition salts include salts of inorganic acids as well as organic acids. Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like.

Unless otherwise specified the reference to any of the compounds disclosed in this application covers the enantiomerically pure compound as well as mixtures of the enantiomers in any ratio.

EXPERIMENTAL

General Experimental

Unless otherwise stated, all reactions were carried out under nitrogen. Reactions were monitored by thin-layer chromatography (TLC) analysis and/or LC-MS. All reagents were purchased and used without further purification. Spots were visualized by exposure to ultraviolet (UV) light (254 nm), or by staining with a 5% w/w solution of phosphomolybdenic acid (PMA) in ethanol or basic aqueous potassium permanganate ($KMnO_4$) and then heating. Column chromatography was carried out using Merck C60 (40-63 μm, 230-240 mesh) silica gel. NMR spectra were recorded at 250, 500 or 600 MHz ($^1$H NMR), and calibrated to the residual solvent peak. The following abbreviations are used for NMR data: s, singlet; d, doublet; t, triplet; m, multiplet. Coupling constants are rounded to nearest 0.5 Hz. Enantiomeric excess was determined by chiral HPLC.

Resolution of racemic compounds can be carried out as disclosed in e.g. WO12/093165 and WO11/003423.

LC-MS Method

Acquity UPLC BEH C18 1.7 μm column; 2.1×50 mm operating at 60° C. with flow 1.2 mL/minute of a binary gradient consisting of water+0.1% formic acid (A) and acetonitrile+5% water+0.1% formic acid (B). UV detection at 254 nm.

Chiral HPLC Method

Phenomenex Lux 5μ Cellulose-2 column; 250×4.6 mm operating at 30° C. with flow 0.5 or 1.0 mL/minute of n-hexane:isopropanol:diethylamine, 90:10:0.1. UV detection at 220 nm.

HPLC Methods

Method 1: Chromolith Performance Rp-18e 2μ column; 100×4.6 mm operating at 30° C. with flow 2.0 mL/minute of water:triethylamine:acetonitrile, 1000:5.5:1000, adjusted to pH 3 with $H_3PO_4$. UV-detection at 254 nm.

Method 2: Agilent Zorbax SB-Phenyl 3.5μ column; 150×4.6 mm operating at 40° C. with flow 1.0 mL/minute. UV-detection at 220 nm. Mobile phase A: water+trifluoroacetic acid=1000+0.5 mL; mobile phase B: acetonitrile+trifluoroacetic acid=1000+0.5 mL. Gradient: 0 min: 90% A, 10% B; 20 min: 5% A, 95% B; 25 min: 5% A, 95% B; 25.1 min: 90% A, 10% B; 30 min: 90% A, 10% B.

Method 3: Phenomenex Luna C18 3.0μ column; 150×4.6 mm operating at 40° C. with flow 1.0 mL/minute. UV-detection at 220 nm. Mobile phase A: 25 mM phosphate buffer pH 7.4:acetonitrile=40:60; mobile phase B: water:acetonitrile=10:90. Gradient: 0 min: 100% A, 0% B; 32 min: 100% A, 0% B; 35 min: 50% A, 50% B; 37 min: 50% A, 50% B; 39 min: 100% A, 0% B; 40 min: 100% A, 0% B.

GC Method

Rtx-5 amine 0.5μ; 30 m×0.25 mm with flow of 1 mL/minute Helium. FID detection (250° C.). Gradient: 0 min: 50° C.; 9 min: 140° C.; 11 min: 140° C.; 21 min: 240° C.; 23 min 240° C.; 26 min: 300° C.; 28 min: 300° C.

Synthesis of Compounds of the Invention

A. Synthesis of 6-chloro-3-(phenyl-$d_5$)-inden-1-one (I)

Scheme 3:

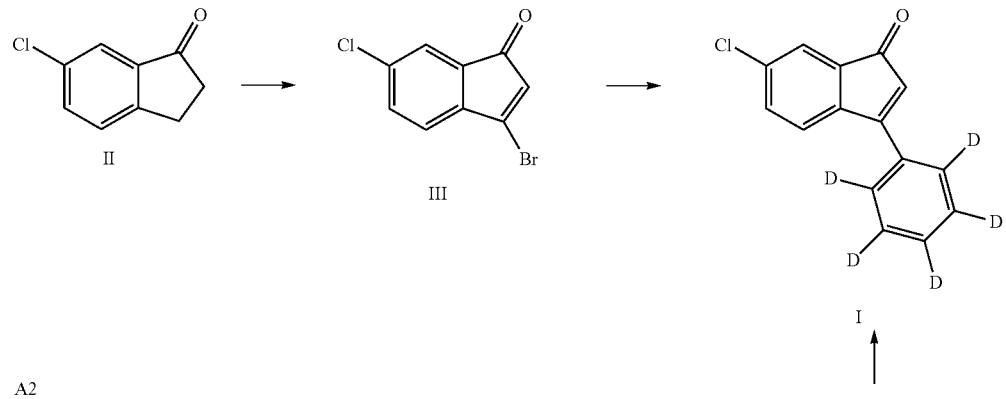

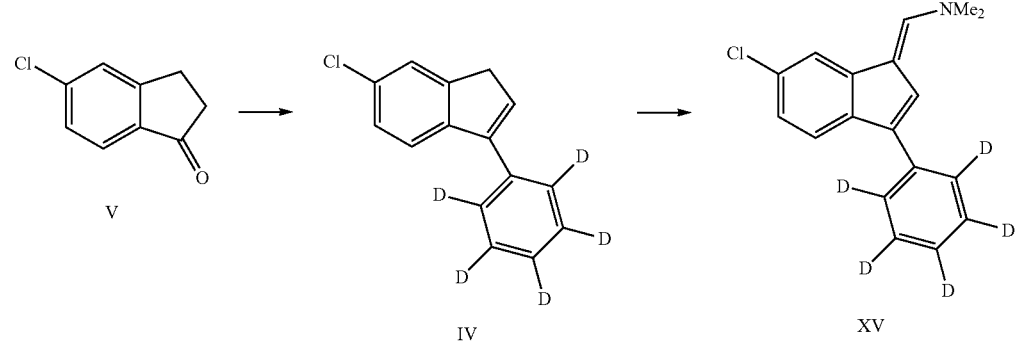

A1. Via Suzuki Reaction (Scheme 3, Route A1)

Synthesis of 3-bromo-6-chloro-inden-1-one (III)

To a solution of 6-chloro-1-indanone (II) (100.0 g, 600.2 mmol) in 1,2-dichloroethane (1.00 L) was added 2,2'-azo-bis-isobutyronitrile (9.86 g, 60.0 mmol) followed by N-bromo-succinimide (224.3 g, 1.26 mol). The reaction mixture was quickly heated to reflux. After 30 min at reflux, more 2,2'- azo-bis-isobutyronitrile (9.86 g, 60.0 mmol) was added. The reaction mixture was kept for 4.5 h at reflux. Afterwards the mixture was stirred at room temperature overnight. The mixture was cooled to 0° C., and triethylamine (126 mL, 904 mmol) was added dropwise. The mixture was stirred for 1 h at 0° C., and then allowed to heat to room temperature. Water (1.0 L) was added. The mixture was vigorously stirred for 15 min. The stirring was stopped, and the aqueous layer was removed by suction. Fresh water (1.0 L) was added, and the mixture was stirred for 15 min. The aqueous layer was then separated by suction. The organic phase was further shaken with brine (500 mL) in a separating funnel.

The organic layer was separated and stirred with $MgSO_4$ and activated charcoal for 30 min. The mixture was filtered through a layer of Celite. The filtrate was evaporated to dryness in vacuo. This yielded crude 3-bromo-6-chloro-inden-1-one (III) (190 g) as a solid, which was used in the next step without further purification.

Synthesis of 6-chloro-3-(phenyl-$d_5$)-inden-1-one (I)

To the crude 3-bromo-6-chloro-inden-1-one (III) from above was added palladium acetate (5.78 g, 25.8 mmol), triphenylphosphine (13.5 g, 51.5 mmol) and 4,4,5,5-tetramethyl-2-$d_5$-phenyl-[1,3,2]dioxaborolane (116 g, 566 mmol) followed by THF (1.50 L) at room temperature. Water (750 mL) and potassium phosphate (115 g, 541 mmol) was added. The reaction mixture was stirred vigorously for 2 h at room temperature. A dark almost black solution formed. Heptane (0.70 L) was added. The organic phase was then washed with water (1.0 L) and brine (0.5 L), dried over $MgSO_4$, filtered and and evaporated to dryness in vacuo. This yielded crude 6-chloro-3-(phenyl-$d_5$)-inden-1-one (I) as a dark solid. The crude 6-chloro-3-(phenyl-$d_5$)-inden-1-one (I) was dissolved in a heptane-EtOAc (2:1) mixture and the solution was filtered through silica gel. The filtrate was evaporated to dryness in vacuo. The residue was reprecipitated from heptane by dissolving in boiling heptane, filtering hot and allowing to cool slowly to room temperature to yield 6-chloro-3-(phenyl-$d_5$)-inden-1-one (I) (75.8 g, 52%) as a dark orange solid, with a purity of 95% according to LC-MS analysis.

Analytical data for 6-chloro-3-(phenyl-$d_5$)-inden-1-one (I):
$^1$H NMR (600 MHz, $CDCl_3$) $\delta_H$ 6.04 (s, 1H), 7.32 (d, J=8.0 Hz, 1H), 7.37 (dd, J=2.0, 8.0 Hz, 1H), 7.49 (dd, J=0.5, 2.0 Hz, 1H); $^{13}$C NMR (150 MHz, $CDCl_3$) $\delta_C$ 122.7, 123.1, 123.5, 127.2 (t, J=23.5 Hz), 128.7 (t, J=23.5 Hz), 130.6 (t, J=23.5 Hz), 132.2, 132.6, 134.2, 134.4 (t, J=23.5 Hz), 135.7, 142.1, 162.8; LC-MS (APPI): m/e calc. for $C_{15}H_5D_5ClO$ [M+H]$^+$ 246.1. found 246.1.

A2. Via Oxidation (Scheme 3, Route A2)

Example 1

Synthesis of 6-chloro-3-(phenyl-$d_5$)-1H-indene (IV)

To a suspension of magnesium (4.43 g, 182 mmol) in THF (15.0 mL) was added Red-Al (0.50 mL, 1.67 mmol, 65% w/w in toluene). A small amount (approximately 5 ml) of a solution of bromobenzene-$d_5$ (29.3 g, 181 mmol) in THF (100 mL) was added at room temperature. The mixture was heated gently (40-50° C.) which gave initiation of the reaction. Initiation of the reaction was detected by an exotherm and the remaining solution of bromobenzene-$d_5$ was added dropwise as to maintain a steady reflux, which took 35 min to complete. Afterwards the mixture was heated at reflux for 1.5 h. The resulting mixture was cooled to room temperature, and the solution was decanted (using cannula) from the excess magnesium. To the solution was added a solution of 5-chloro-1-indanone (V) (20.0 g, 120.0 mmol) in THF (100 mL) over a period of 30 min, which kept the temperature below 50° C. (no external heating or cooling). Upon completion of addition, the reaction mixture was allowed to stir for 1 h (no external heating or cooling). Concentrated sulfuric acid (13.3 mL, 96% w/w) was added very slowly and carefully while maintaining a temperature below 50° C. in the reaction mixture. Once the addition was finished, water (125 mL) was added. Most of the THF was removed by evaporation in vacuo. The remaining aqueous mixture was extracted with heptane twice (2×100 mL). The combined extracts were washed with saturated aq. $NaHCO_3$-solution (100 mL), water (2×100 mL) and brine (100 mL). The organic phase was stirred vigorously with $MgSO_4$ and activated charcoal for 20 min, and filtered through a layer of Celite. The filtrate was evaporated to dryness. The residue was co-evaporated with ethanol to dryness in vacuo to remove most heptane by azeotrop distillation. This yielded crude 6-chloro-3-(phenyl-$d_5$)-1H-indene (IV) (26.7 g) as a solid. The crude product was reprecipitated from ethanol by dissolving in a minimum amount of boiling ethanol and cooling slowly to 5° C. with stirring to afford 6-chloro-3-(phenyl-$d_5$)-1H-indene (IV) (20.5 g, 74%) as a yellowish solid, with a purity of 99% according to LC-MS analysis.

Analytical data for 6-chloro-3-(phenyl-$d_5$)-1H-indene (IV):
$^1$H NMR (600 MHz, $CDCl_3$) $\delta_H$ 3.49 (d, J=2.0 Hz, 2H), 6.57 (t, J=2.0 Hz, 1H), 7.29 (dd, J=2.0, 8.0 Hz, 1H), 7.48 (d, J=8.0 Hz, 1H), 7.50 (m, 1H); $^{13}$C NMR (150 MHz, $CDCl_3$) $\delta_C$ 38.1, 121.2, 124.6, 126.5, 127.3 (t, J=24.0 Hz), 127.4 (t, J=24.0 Hz), 128.3 (t, J=24.0 Hz), 131.1, 131.2, 135.6, 142.6, 144.7, 146.6; LC-MS (APPI): m/e calc. for $C_{15}H_6D_5Cl$ (M$^+$) 231.1. found 231.1.

Synthesis of 6-chloro-3-(phenyl-$d_5$)-inden-1-one (I)

To a solution of 6-chloro-3-(phenyl-$d_5$)-1H-indene (3.00 g, 12.9 mmol) in THF (30.0 mL) was added 1,1-dimethoxy-N,N-dimethylmethanamine (4.30 mL, 32.4 mmol) at room temperature. The mixture was heated at 45° C. for 2.5 h. Water (15.0 mL) followed by sodium metaperiodate (8.31 g, 38.8 mmol) was added. The mixture was further heated at 60° C. with vigorous stirring for 1.5 h. The mixture was filtered through a layer of Celite. The filtercake was washed thoroughly with dichloromethane. The combined filtrates were washed with brine, dried over $MgSO_4$, filtered and evaporated to dryness in vacuo. The residue was purified by column chromatography eluting with heptane-EtOAc (20:1) mixture to afford 6-chloro-3-(phenyl-$d_5$)-inden-1-one (I) (2.86 g, 90%) as a yellow-orange solid, with a purity of 97% according to LC-MS analysis.

Analytical data (NMR and LC-MS) for compound (I) were the same as those reported above.

Example 2

Synthesis of (E)-1-(6-chloro-3-phenyl($d_5$)-1H-inden-1-ylidenemethyl)-N,N-dimethylamine (XIX)

Magnesium turnings (5.60 kg, 230 mol) were suspended in 2-MeTHF (21.3 L). Isopropylmagnesium chloride (25 mL, 50.0 mmol, 2 M) in THF was added to the magnesium turnings and the magnesium turnings suspension was warmed to reflux with stirring. A solution of bromobenzene-$d_5$ (34.23 kg, 211 mol) in 2-MeTHF (79.6 L) was added to the magnesium turnings over a period of 1 h 3 min. 2-MeTHF (10.5 L) was added and the reaction was refluxed for 38 min. The reaction was then cooled to 22° C. before a solution of 5-chloro-1-indanone (V) (32.5 kg, 195 mol) dissolved in 2-MeTHF (198 L) was added over a period of 42 min, with a maximum temperature of 44° C. 2-MeTHF (10.5 L) was added and the reaction was stirred overnight. Aq. HCl-solution (80 L, 15% w/w) was added to the reaction, and the reaction was stirred for 2 h 46 min. The phases were separated and the organic phase was washed with aq. NaCl-solution (40 L, 15% w/w). The phases were separated and the organic phase was reduced in volume by distillation to 170 L. The reaction was cooled to 30° C. and then 1,1-dimethoxy-N,N-dimethylmethanamine (31.0 kg, 260 mol) was added. The reaction was stirred overnight and then cooled to 6° C. The formed precipitate was filtered off and washed with heptane twice (2×38 L). The resulting solid was dried in a vacuum oven at 50° C. for two days to yield (E)-1-(6-chloro-3-phenyl (d$_5$)-1H-inden-1-ylidene)-N,N-dimethylmethanamine (XIX) (48.0 kg, 86%) with a purity of >99% according to HPLC analysis (method 1).

Analytical data for (E)-1-(6-chloro-3-phenyl(d$_5$)-1H-inden-1-ylidenemethyl)-N,N-dimethylamine (XIX):

$^1$H NMR (250 MHz, CDCl$_3$) δ$_H$ 3.26 (s, 6H), 7.11 (s, 1H), 7.12 (dd, J=2.0, 8.5 Hz, 1H), 7.37 (s, 1H), 7.58 (d, J=2.0 Hz, 1H), 7.66 (d, J=8.0 Hz, 1H).

Synthesis of 6-chloro-3-(phenyl-d$_5$)-inden-1-one (I)

A mixture of (E)-1-(6-chloro-3-phenyl-1H-inden-1-ylidenemethyl)-N,N-dimethylamine (XIX) (803 g, 2.80 mol), sodium metaperiodate (1.80 kg, 8.40 mol), THF (3.9 L) and water (3.9 L) was stirred at 30° C. After 48 min the exotherm from the reaction had warmed the mixture to 36° C., the maximum temperature reached during the reaction. The reaction was stirred overnight at 30° C. and then cooled to 21° C. Toluene (280 mL), methanesulfonic acid (546 mL) and heptane (4.2 L) were added and the reaction was warmed to 29° C. The phases were separated and the organic phase was washed with water (2×4 L). Heptane (4 L) was added to the organic phase and the volume of the organic phase was reduced by distillation in vacuo (max. 45° C.) to 3 L. THF (280 mL) and heptane (4 L) were added, and the reaction was stirred overnight. The reaction was cooled to 5° C. for 2 h before the formed precipitate was filtered off and washed with heptane (2.5 L). The solid was dried in a vacuum oven at 40° C. overnight to yield 6-chloro-3-(phenyl-d$_5$)-inden-1-one (I) (508 g, 74%) with a purity of >99% according to HPLC analysis (method 1).

Analytical data (NMR and LC-MS) for compound (I) were the same as those reported above.

B. Synthesis of (±)-6-chloro-3-(phenyl-d$_5$)-1H-inden-1-ol (VI)

Scheme 4:

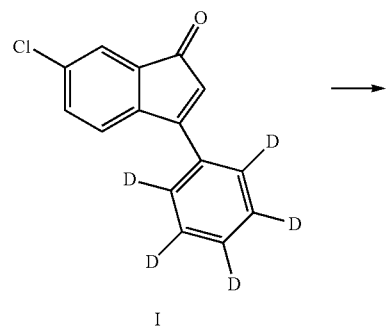

I

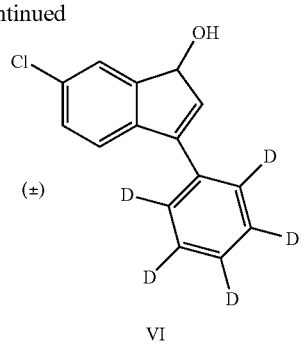

VI

To a solution of 6-chloro-3-(phenyl-d$_5$)-inden-1-one (I) (1.00 g, 4.07 mmol) in THF (10.0 mL) was added over a period of 45 min diisobutylaluminium hydride in THF (5.70 mL, 5.70 mmol, 1.0 M) at −10° C. with stirring. The resulting reaction mixture was stirred for 30 min at −10° C. Methanol (3.0 mL) was added at −10° C., and the cooling was removed. After 5 min saturated aq. potassium sodium tartrate solution (10 mL) was added. The resulting mixture was stirred for 15 min, and saturated aq. NH$_4$Cl-solution (5 mL) was added followed by dichloromethane (30 mL). The organic layer was separated, and washed with brine. The organic layer was dried over MgSO$_4$, filtered and evaporated to dryness in vacuo.

The residue was purified by column chromatography eluting with heptane-EtOAc (4:1) to afford (±)-6-chloro-3-(phenyl-d$_5$)-1H-inden-1-ol (VI) (907 mg, 90%) as an off-white solid, with a purity of 98% according to LC-MS analysis.

Analytical data for (±)-6-chloro-3-(phenyl-d$_5$)-1H-inden-1-ol (VI):

$^1$H NMR (600 MHz, CDCl$_3$) δ$_H$ 5.18 (dd, J=2.0, 7.0 Hz, 1H), 5.76 (d, J=7.0 Hz, 1H), 6.55 (d, J=2.0 Hz, 1H), 7.36 (dd, J=2.0, 8.0 Hz, 1H), 7.42 (d, J=8.0 Hz, 1H), 7.53 (m, 1H); $^{13}$C NMR (150 MHz, CDCl$_3$) δ$_C$ 74.8, 121.7, 124.3, 127.0 (t, J=24.0 Hz), 127.8, 128.1 (t, J=24.0 Hz), 128.6 (t, J=24.0 Hz), 131.1, 134.1, 136.5, 140.2, 142.4, 150.5; LC-MS (APPI): m/e calc. for C$_{15}$H$_7$D$_5$ClO [M+H]$^+$ 248.1. found 248.2.

C. Synthesis of (S)-6-chloro-3-(phenyl-d$_5$)-1H-inden-1-ol (VII)

Scheme 5:

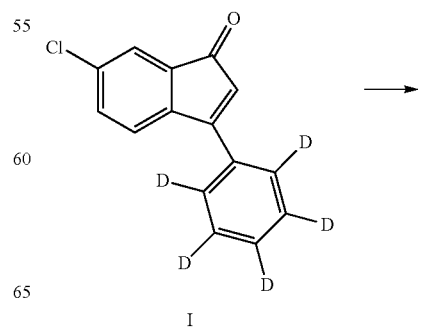

I

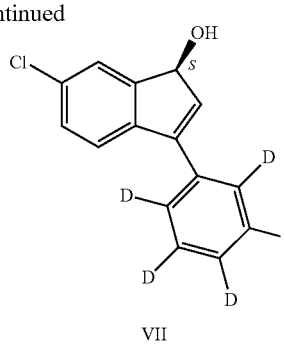

VII

To a solution of (R)-(+)-2-methyl-CBS-oxazaborolidine in THF (61 μL, 61 μmol, 1.0 M) was added THF (4.0 mL) followed by a solution of borane-THF complex in THF (1.34 mL, 1.34 mmol, 1.0 M). The resulting solution was cooled to −10° C., and a solution of 6-chloro-3-(phenyl-d$_5$)-inden-1-one (I) (300 mg, 1.22 mmol) in THF (4.0 mL) was added slowly over a period of 1.5 h. The reaction mixture was stirred for a further 45 min at −10° C. Methanol (5 mL) was added to quench the reaction, and the mixture was allowed to warm to room temperature. The mixture was co-evaporated with silica gel. The obtained material was loaded onto a silica gel column and elution with heptane-EtOAc (4:1) afforded (S)-6-chloro-3-(phenyl-d$_5$)-1H-inden-1-ol (VII) (243 mg, 80%) as a white solid, with 97% ee according to chiral HPLC analysis.

Analytical data (NMR and LC-MS) for compound (VII) were the same as those reported above for compound (VI).

D. Synthesis of (±)-6-chloro-3-(phenyl-d$_5$)-indan-1-one (VIII)

D1. Via Hydrogenation

Scheme 6:

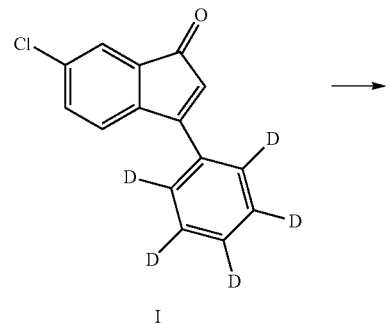

I

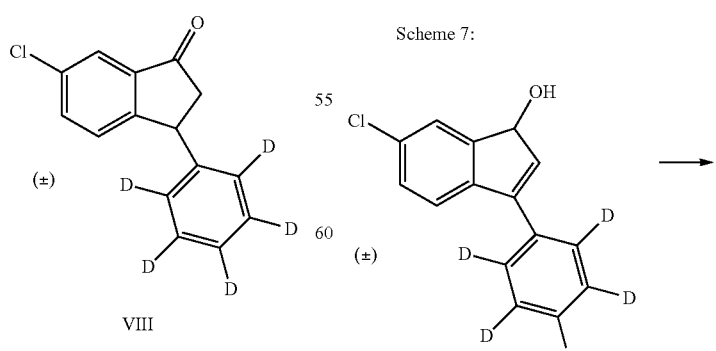

VIII

General Method:

To a solid mixture of 6-chloro-3-(phenyl-d$_5$)-inden-1-one (I) (200 mg, 0.814 mmol) and tris(triphenylphosphine)rhodium(I) chloride (7.5 mg, 8.1 μmol) was added solvent (3.0 mL, see Table 1. for details). The resulting solution was hydrogenated at 4 bar hydrogen gas for 22 h at room temperature. The reaction mixture was evaporated onto silica gel, loaded onto a silica gel column and elution with heptane-EtOAc (20:1) afforded (±)-6-chloro-3-(phenyl-d$_5$)-indan-1-one (VIII). The obtained compound (VIII) was analysed by LC-MS, see Table 1 for details.

TABLE 1

| Screening of solvents:[1] | | |
|---|---|---|
| Entry | Solvent | LC-MS yield/%[2] |
| 1 | Methanol | 15 |
| 2 | Toluene | 25 |
| 3 | EtOAc | 70 |

[1]Reaction conditions: (Ph$_3$P)$_3$RhCl (1 mol %), hydrogen gas (4 bar), room temperature, 22 h.
[2]UV area percentage in LC-MS.

Example

To a solid mixture of 6-chloro-3-(phenyl-d$_5$)-inden-1-one (I) (200 mg, 0.814 mmol) and tris(triphenylphosphine)rhodium(I) chloride (7.5 mg, 8.1 μmol) was added EtOAc (3.0 mL). The resulting solution was hydrogenated at 4 bar hydrogen gas for 22 h at room temperature. The reaction mixture was evaporated onto silica gel, loaded onto a silica gel column and elution with heptane-EtOAc (20:1) afforded (±)-6-chloro-3-(phenyl-d$_5$)-indan-1-one (VIII) (164 mg, 81%).

Analytical data for (±)-6-chloro-3-(phenyl-d$_5$)-inden-1-one (VIII):

$^1$H NMR (500 MHz, CDCl$_3$) δ$_H$ 2.72 (dd, 1H, J=4.0, 19.5 Hz), 3.27 (dd, 1H, J=8.0, 19.5 Hz), 4.55 (dd, 1H, J=4.0, 8.0 Hz), 7.21 (d, 1H; J=8.0 Hz), 7.52 (dd, 1H, J=2.0, 8.0 Hz), 7.77 (d, 1H, J=2.0 Hz); $^{13}$C NMR (125 MHz, CDCl$_3$) δ$_C$ 44.0, 47.2, 123.2, 126.8 (t, J=24.0 Hz), 127.3 (t, J=24.0 Hz), 128.7 (t, J=24.0 Hz), 134.4, 135.1, 138.2, 142.9, 156.0, 206.4; LC-MS (APPI): m/e calc. for C$_{15}$H$_7$D$_5$ClO [M+H]$^+$ 248.1. found 247.6.

D2. Via Rearrangement

Scheme 7:

VI

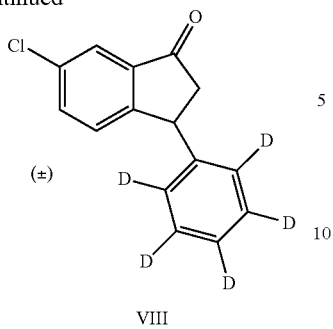

VIII

To a solution of (±)-6-chloro-3-(phenyl-d₅)-1H-inden-1-ol (VI) (200 mg, 0.807 mmol) and DABCO (1,4-diazabicyclo[2.2.2]octane) (45.3 mg, 0.404 mmol) in THF (3.0 mL) was added triethylamine (281 µL, 2.02 mmol) at room temperature. The reaction mixture was heated at 60° C. for 1 h. The reaction mixture was cooled and co-evaporated with silica gel. The obtained material was loaded onto a silica gel column and elution with heptane-EtOAc (10:1) afforded (±)-6-chloro-3-(phenyl-d₅)-indan-1-one (VIII) (188 mg, 94%).

Analytical data (NMR and LC-MS) for compound (VIII) were the same as those reported above.

E. Synthesis of (S)-6-chloro-3-(phenyl-d₅)-indan-1-one (IX)

E1. Via Rearrangement

Scheme 8:

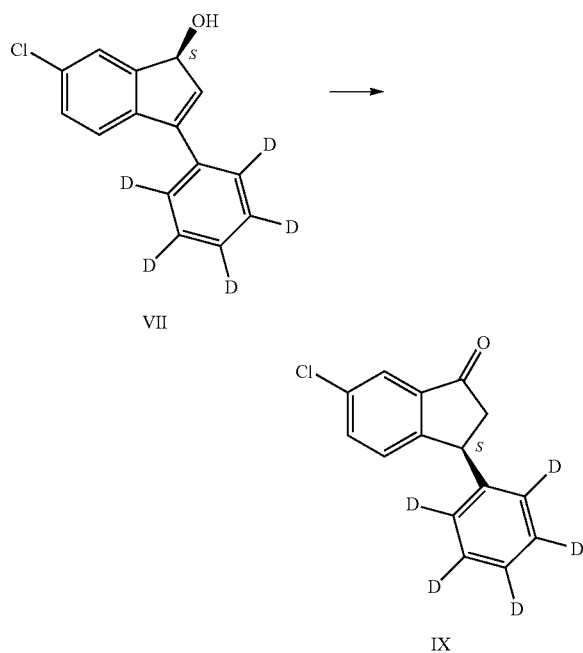

To a solution of (S)-6-chloro-3-(phenyl-d₅)-1H-inden-1-ol (VII) (200 mg, 0.807 mmol, 97% ee) and DABCO (45.3 mg, 0.404 mmol) in THF (3.0 mL) was added triethylamine (281 µL, 2.02 mmol) at room temperature. The reaction mixture was heated at 60° C. for 1 h. The reaction mixture was cooled and co-evaporated with silica gel. The obtained material was loaded onto a silica gel column and elution with heptane-EtOAc (10:1) afforded (S)-6-chloro-3-(phenyl-d₅)-indan-1-one (IX) (188 mg, 94%), with 80% ee according to chiral HPLC analysis.

Analytical data (NMR and LC-MS) for compound (IX) were the same as those reported above for compound (VIII).

E2. Via Organocatalytic Asymmetric Transfer Hydrogenation

Scheme 9:

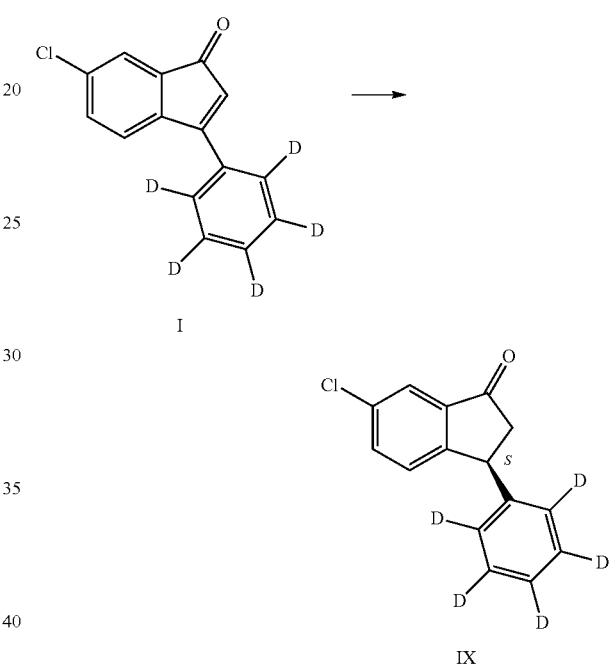

General Method:

To a solution of 6-chloro-3-(phenyl-d₅)-inden-1-one (I) (300 mg) in a solvent was added catalyst and reductant at room temperature or 60° C. (see Table 2. for details). The reaction mixture was stirred for 10-24 h. The reaction mixture was evaporated onto silica gel, loaded onto a silica gel column and elution with heptane-EtOAc (20:1) afforded (S)-6-chloro-3-(phenyl-d₅)-indan-1-one (IX).

TABLE 2

| Screening of reaction conditions: | | | |
| --- | --- | --- | --- |
| Entry | Conditions[1,2,3] | Isolated yield/% | ee (sense)/%[4] |
| 1 | 1 (30 mol %), TCA (30 mol %), 5, Et₂O, room temperature[5] | 65 | 10 (S) |
| 2 | 2 (30 mol %), TCA (30 mol %), 5, Et₂O, room temperature[5] | 65 | 6 (S) |
| 3 | 3 (30 mol %), TCA (30 mol %), 5, Et₂O, room temperature[5] | 44 | 8 (S) |

TABLE 2-continued

Screening of reaction conditions:

| Entry | Conditions[1,2,3] | Isolated yield/% | ee (sense)/%[4] |
|---|---|---|---|
| 4 | 4 (5 mol %), 6, Bu$_2$O, 60° C.[6] | 95 | 46 (R) |

1. TCA = trichloroacetic acid; Et$_2$O = diethyl ether; Bu$_2$O = dibutyl oxide
2. Catalysts:

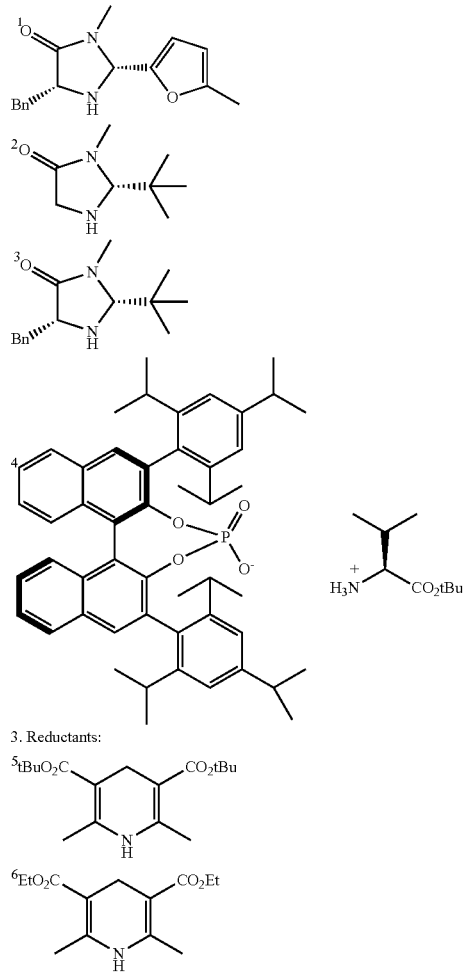

3. Reductants:

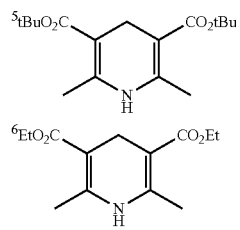

4. From analysis of the reaction mixture by chiral HPLC.
5. Jamison B. Tuttle et al, *J. Am. Chem. Soc.* 2006, 128, 12662-12663.
6. Nolwenn J. A. Martin et al, *J. Am. Chem. Soc.* 2006, 128, 13368-13369.

Example

The catalyst 4 was made by mixing equimolar amounts of (R)-TRIP and L-valine tert-butyl ester in Et$_2$O. The formed precipitate was filtered off and dried in vacuo to yield catalyst 4.

To a solid mixture of 6-chloro-3-(phenyl-d$_5$)-inden-1-one (I) (300 mg, 1.22 mmol), reductant 6 (402 mg, 1.59 mmol) and catalyst 4 (57 mg, 0.0610 mmol) was added Bu$_2$O at room temperature. The reaction mixture was heated at 60° C. for 10 h. The reaction mixture was co-evaporated with silica gel, loaded onto a silica gel column and elution with heptane-EtOAc (20:1 to 10:1) afforded (S)-6-chloro-3-(phenyl-d$_5$)-indan-1-one (IX) (287 mg, 95%), with 46% ee according to chiral HPLC analysis.

Analytical data (NMR and LC-MS) for compound (IX) were the same as those reported above for compound (VIII).

E3. Via Asymmetric Hydrogenation (Scheme 9)

General Method:

To a solid mixture of metal precursor and ligand, or catalyst was added solvent. The mixture was stirred vigorously for 30 min at room temperature, after which a solution of 6-chloro-3-(phenyl-d$_5$)-inden-1-one (I) in solvent was added (see Table 3-6, for details). The resulting mixture was hydrogenated at 4 bar hydrogen gas with stirring for 18-70 h at room temperature. The reaction mixture was analysed directly by LC-MS and chiral HPLC. The product (S)-6-chloro-3-(phenyl-d$_5$)-indan-1-one (IX) could be isolated evaporation of the reaction mixture in vacuo and purification by column chromatography eluting with heptane-EtOAc (20:1), or reprecipitation from ethanol.

TABLE 3

Initial screening of reaction conditions:[1]

| Entry | Metal precursor[2] | Ligand/ catalyst[2] | Solvent[6] | LC-MS yield/ %[3] | Isolated yield/ %[4] | ee (sense)/ %[5] |
|---|---|---|---|---|---|---|
| 1 | 7 | 11 | DCE | 8 | ND | ND |
| 2 | 7 | 12 | DCE | Trace | ND | ND |
| 3 | 7 | 13 | DCE | 45 | 59 | 21 (R) |
| 4 | 7 | 14 | DCE | 52 | ND | 26 (R) |
| 5 | 7 | 15 | DCE | 9 | ND | 19 (S) |
| 6 | 7 | 16 | DCE | Trace | ND | ND |
| 7 | 7 | 17 | DCE | 20 | 47 | <5 |
| 8 | 7 | 18 | DCE | 47 | 66 | <5 |
| 9 | 7 | 19 | DCE | 40 | 50 | <5 |
| 10 | 7 | 20 | DCE | Trace | ND | ND |
| 11 | 7 | 21 | DCE | 45 | ND | <5 |
| 12 | 7 | 22 | DCE | 33 | ND | <5 |
| 13 | 7 | 23 | DCE | 45 | ND | <5 |
| 14 | 7 | 24 | DCE | 24 | ND | <5 |
| 15 | 7 | 13 | MeOH | 7 | ND | ND |
| 16 | 7 | 14 | MeOH | 3 | ND | ND |
| 17 | 7 | 25 | MeOH | 4 | ND | ND |
| 18 | 8 | 11 | DCE | 4 | ND | ND |
| 19 | 8 | 12 | DCE | 3 | ND | ND |
| 20 | 8 | 13 | DCE | 46 | ND | 34 (R) |
| 21 | 8 | 14 | DCE | 7 | ND | ND |
| 22 | 8 | 15 | DCE | 0 | ND | ND |
| 23 | 8 | 16 | DCE | 0 | ND | ND |
| 24 | — | 26 | DCE | 0 | ND | ND |
| 25 | — | 27 | DCE | 0 | ND | ND |
| 26 | — | 28 | DCE | 0 | ND | ND |
| 27 | 8 | 20 | DCE | 0 | ND | ND |
| 28 | 8 | 17 | DCE | 4 | ND | ND |
| 29 | 8 | 22 | DCE | 3 | ND | ND |
| 30 | 8 | 23 | DCE | 0 | ND | ND |
| 31 | 8 | 24 | DCE | 0 | ND | ND |
| 32 | 8 | 18 | DCE | 14 | ND | ND |
| 32 | 8 | 21 | DCE | 0 | ND | ND |
| 33 | — | 29 | MeOH | 0 | ND | ND |
| 34 | — | 30 | MeOH | 0 | ND | ND |
| 35 | 9 | 11 | DCE | 36 | ND | <5 |
| 36 | 9 | 12 | DCE | 64 | ND | <5 |
| 37 | 9 | 13 | DCE | 67 | ND | <5 |
| 38 | 9 | 14 | DCE | 88 | ND | <5 |
| 39 | 9 | 20 | DCE | 2 | ND | ND |
| 40 | 9 | 17 | DCE | 9 | ND | ND |
| 41 | 9 | 22 | DCE | 28 | ND | <5 |
| 42 | 9 | 23 | DCE | 16 | ND | <5 |
| 43 | 9 | 24 | DCE | 22 | ND | <5 |
| 44 | 9 | 15 | DCE | 14 | ND | <5 |
| 45 | 9 | 16 | DCE | 31 | ND | <5 |
| 46 | 9 | 18 | DCE | 6 | ND | ND |
| 47 | 9 | 21 | DCE | 2 | ND | ND |
| 48 | 9 | 11 | MeOH | 7 | ND | <5 |
| 49 | 9 | 12 | MeOH | 21 | ND | <5 |
| 50 | 9 | 13 | MeOH | 34 | ND | <5 |
| 51 | 9 | 14 | MeOH | 40 | ND | <5 |
| 52 | 9 | 20 | MeOH | 17 | ND | <5 |
| 53 | 9 | 17 | MeOH | 18 | ND | <5 |

TABLE 3-continued

Initial screening of reaction conditions:[1]

| Entry | Metal precursor[2] | Ligand/catalyst[2] | Solvent[6] | LC-MS yield/%[3] | Isolated yield/%[4] | ee (sense)/%[5] |
|---|---|---|---|---|---|---|
| 54 | 9 | 22 | MeOH | 27 | ND | <5 |
| 55 | 9 | 23 | MeOH | 27 | ND | <5 |
| 56 | 9 | 24 | MeOH | 10 | ND | ND |
| 57 | 9 | 15 | MeOH | 42 | ND | <5 |
| 58 | 9 | 16 | MeOH | 6 | ND | ND |
| 59 | 9 | 18 | MeOH | 9 | ND | <5 |
| 60 | 9 | 21 | MeOH | 3 | ND | ND |
| 61 | 9 | 11 | TFE | 67 | ND | <5 |
| 62 | 9 | 14 | TFE | 70 | ND | <5 |
| 63 | 10 | 11 | MeOH | 46 | ND | 10 (R) |
| 64 | 10 | 12 | MeOH | 65 | ND | 22 (S) |
| 65 | 10 | 13 | MeOH | 59 | ND | 20 (R) |
| 66 | 10 | 14 | MeOH | 34 | ND | 22 (S) |
| 67 | 10 | 15 | MeOH | 53 | ND | 12 (S) |
| 68 | 10 | 16 | MeOH | 0 | ND | ND |
| 69 | 10 | 17 | MeOH | 35 | ND | 16 (S) |
| 70 | 10 | 18 | MeOH | 50 | ND | 41 (S) |
| 71 | 10 | 20 | MeOH | 5 | ND | ND |
| 72 | 10 | 21 | MeOH | 32 | ND | 24 (S) |
| 73 | 10 | 22 | MeOH | 65 | ND | 9 (S) |
| 74 | 10 | 31 | MeOH | 9 | ND | ND |
| 75 | 10 | 23 | MeOH | 38 | ND | 12 (S) |
| 76 | 10 | 24 | MeOH | 64 | ND | 26 (R) |
| 77 | 10 | 32 | MeOH | 63 | ND | 5 (S) |
| 78 | 10 | 33 | MeOH | 5 | ND | ND |
| 79 | 10 | 25 | MeOH | 25 | ND | 29 (R) |
| 80 | 10 | 34 | MeOH | 1 | ND | ND |
| 81 | 10 | 35 | MeOH | 75 | ND | <5 |
| 82 | 10 | 36 | MeOH | 38 | ND | 60 (S) |
| 83 | 10 | 37 | MeOH | 34 | ND | 28 (S) |
| 84 | 10 | 38 | MeOH | 46 | ND | 29 (S) |
| 85 | 10 | 11 | MeOH | 46 | ND | 10 (R) |
| 86 | 10 | 11 | DCE | 51 | 57 | 30 (S) |
| 87 | 10 | 12 | DCE | 33 | ND | 24 (R) |
| 88 | 10 | 13 | DCE | 44 | ND | 28 (S) |
| 89 | 10 | 14 | DCE | 61 | 50 | 48 (S) |
| 90 | 10 | 15 | DCE | 11 | ND | ND |
| 91 | 10 | 16 | DCE | 0 | ND | ND |
| 92 | 10 | 17 | DCE | 20 | ND | 46 (R) |
| 93 | 10 | 18 | DCE | 53 | ND | 49 (S) |
| 94 | 10 | 20 | DCE | 60 | 34 | 62 (S) |
| 95 | 10 | 21 | DCE | 38 | ND | 24 (S) |
| 96 | 10 | 22 | DCE | 11 | ND | ND |
| 97 | 10 | 39 | DCE | 17 | 55 | 18 (S) |
| 98 | 10 | 23 | DCE | 51 | ND | 34 (S) |
| 99 | 10 | 24 | DCE | 54 | 73 | 63 (R) |
| 100 | 10 | 32 | DCE | 61 | ND | 37 (S) |
| 101 | 10 | 33 | DCE | 6 | ND | ND |
| 102 | 10 | 25 | DCE | 11 | ND | ND |
| 103 | 10 | 34 | DCE | 3 | ND | ND |
| 104 | 10 | 35 | DCE | 24 | ND | 62 (S) |
| 105 | 10 | 36 | DCE | 22 | ND | 37 (S) |
| 106 | 10 | 37 | DCE | 48 | ND | 33 (R) |
| 107 | 10 | 38 | DCE | 13 | ND | ND |
| 108 | 10 | 14 | THF | 11 | ND | 70 (S) |
| 109 | 10 | 18 | THF | 36 | ND | ND |
| 110 | 10 | 11 | EtOAc | 30 | ND | 32 (S) |
| 111 | 10 | 12 | EtOAc | 34 | ND | <5 |
| 112 | 10 | 13 | EtOAc | 43 | ND | 23 (S) |
| 113 | 10 | 14 | EtOAc | 59 | ND | 52 (S) |
| 114 | 10 | 18 | EtOAc | 68 | ND | 57 (S) |
| 115 | 10 | 39 | EtOAc | 73 | ND | 61 (R) |
| 116 | 10 | 20 | EtOAc | 40 | ND | 89 (S) |
| 117 | 10 | 21 | EtOAc | 40 | ND | 13 (S) |
| 118 | 10 | 22 | EtOAc | 17 | ND | 26 (S) |
| 119 | 10 | 23 | EtOAc | 58 | ND | 13 (S) |
| 120 | 10 | 24 | EtOAc | 40 | ND | 57 (R) |
| 121 | 10 | 32 | EtOAc | 54 | ND | 45 (S) |
| 122 | 10 | 33 | EtOAc | 7 | ND | ND |
| 123 | 10 | 25 | EtOAc | 21 | ND | 22 (S) |
| 124 | 10 | 34 | EtOAc | 3 | ND | 30 (S) |
| 125 | 10 | 35 | EtOAc | 75 | ND | 62 (S) |
| 126 | 10 | 36 | EtOAc | 32 | ND | 48 (S) |
| 127 | 10 | 37 | EtOAc | 45 | ND | <5 |
| 128 | 10 | 38 | EtOAc | 9 | ND | ND |
| 129 | 10 | 40 | EtOAc | 5 | ND | ND |
| 130 | 10 | 41 | EtOAc | 5 | ND | ND |

[1]Reaction conditions: Substrate/Rh molar ratio = 50; Ligand/Rh molar ratio = 1; 200 mg 6-chloro-3-(phenyl-$d_5$)-inden-1-one (I); 3 mL solvent; 4 bar hydrogen gas; room temperature; 18-70 h.
[2]Metal precursors and ligands/catalysts:
7: (COD)$_2$IrBAr$_F$, cas # 666826-16-0.
8: (Me-allyl)$_2$(COD)Ru, cas # 12289-94-0.
9: Pd(OCOCF$_3$)$_2$, cas # 42196-31-6.
10: (NBD)$_2$RhBF$_4$, cas # 36620-11-8.
11: (R)-BINAP cas # 76189-55-4.
12: (S)-T-BINAP, cas # 100165-88-6.
13: (R)-DM-BINAP, cas # 137219-86-4.
14: (R)-DTBM-SEGPHOS, cas # 566940-03-2.
15: (R)-Monophos, cas # 157488-65-8.
16: (S,R,R)-(+)-(3,5-Dioxa-4-phosphacyclohepta[2,1-a: 3,4-a']dinaphthalen-4-yl)bis(1-phenylethyl)amine, cas # 415918-91-1.
17: ((1R,1'R,2S,2'S)-Duanphos), cas # 528814-26-8.
18: (S)-Phanephos, cas # 192463-40-4.
19: [((4R,5R)—Ph$_2$-Ubaphox)Ir(COD)]BAr$_F$, cas # 880262-16-8.
20: (S)—Me-f-Ketalphos, cas # 488760-58-3.
21: (R,R)-DIOP, cas # 32305-98-9.
22: (S,S)—Me-Duphos, cas # 136735-95-0.
23: (R)-Prophos, cas # 67884-32-6.
24: (S,S)-Chiraphos, cas # 64896-28-2.
25: (R)—C3-TunePhos, cas # 301847-89-2.
26: RuCl$_2$[(R)-BINAP][(S)-DAIPEN]
27: RuCl$_2$[(S)-(DM-BINAP)][(S)-DAIPEN], cas # 220114-01-2.
28: RuCl(p-cymene)[(S,S)-Ts-DPEN], cas # 192139-90-5.
29: [(R)-BINAP]RuCl$_2$p-cymene, cas # 145926-28-9.
30: [(S)-BINAP]RuCl$_2$, cas # 134524-84-8.
31: (S,S)—Et-Duphos, cas # 136779-28-7.
32: (R)—Me-BoPhoz, cas # 406680-94-2.
33: (S)-BINAPINE, cas # 528854-26-4.
34: (R,R)—Et-BPE, cas # 136705-62-9.
35: Taniaphos SL-T001-1, cas # 1003012-96-1.
36: Walphos SL-W001-1, cas # 387868-06-6.
37: Josiphos SL-J001-1, cas # 155806-35-2.
38: (S,S',R,R')-Tangphos, cas #470480-32-1.
39: (R)-Xylyl-Phanephos, cas # 325168-89-6.
40: (R)-DM-SEGPHOS, cas # 850253-53-1.
41: (R)-SEGPHOS, cas # 244261-66-3.
[3]UV area percentage in LC-MS.
[4]The product was isolated by column chromatography on silica gel.
ND = not determined.
[5]From analysis of the reaction mixture by chiral HPLC.
[6]Solvents used:
DCE = 1,2-dichloroethane
MeOH = methanol
TFE = 2,2,2-trifluoroethanol
THF = tetrahydrofuran
EtOAc = ethyl acetate Optimisation with Four Lead Ligands:

TABLE 4

Influence of ligand/rhodium ratio:[1]

| Entry | Ligand[2] | Ligand/Rh ratio | LC-MS yield/%[3] | ee (sense)/%[4] |
|---|---|---|---|---|
| 1 | 18 | 1 | 65 | 69 (S) |
| 2 | 18 | 2 | 70 | 84 (S) |
| 3 | 18 | 3 | 70 | 86 (S) |
| 4 | 39[5] | 1 | 73 | 61 (R) |
| 5 | 39 | 2 | 74 | 73 (R) |
| 6 | 39 | 3 | 76 | 74 (R) |
| 7 | 35 | 1 | 71 | 70 (S) |
| 8 | 35 | 2 | 64 | 71 (S) |
| 9 | 35 | 3 | 60 | 74 (S) |

TABLE 4-continued

Influence of ligand/rhodium ratio:[1]

| Entry | Ligand[2] | Ligand/Rh ratio | LC-MS yield/%[3] | ee (sense)/%[4] |
|---|---|---|---|---|
| 10 | 14 | 1 | 59 | 52 (S) |
| 11 | 14 | 3 | 6 | ND |

[1]Reaction conditions: 1 mol % (NBD)$_2$RhBF$_4$; ligand; 200 mg 6-chloro-3-(phenyl-d$_5$)-inden-1-one (I); 3 mL EtOAc; hydrogen gas (4 bar); room temperature; 18 h.
[2]Numbers refers in to numbering in Table 3.
[3]UV area percentage in LC-MS.
[4]From analysis of the reaction mixture by chiral HPLC.
[5]2 mol % (NBD)$_2$RhBF$_4$.

Optimisation with (S)-Phanephos:

TABLE 5

Solvent screen:[1]

| Entry | Solvent[4] | LC-MS yield/%[2] | ee (sense)/%[3] |
|---|---|---|---|
| 1 | TBME | 29 | 84 (S) |
| 2 | Toluene | 65 | 87 (S) |
| 3 | Acetone | ~43 | 74 (S) |
| 4 | i-PrOAc | 64 | 84 (S) |
| 5 | EtOAc | 70 | 84 (S) |

[1]Reaction conditions: 1 mol % (NBD)$_2$RhBF$_4$; 3 mol % (S)-Phanephos; 200 mg 6-chloro-3-(phenyl-d$_5$)-inden-1-one (I); 3 mL solvent; hydrogen gas (4 bar); room temperature; 18 h.
[2]UV area percentage in LC-MS.
[3]From analysis of the reaction mixture by chiral HPLC.
[4]Solvents used:
TBME = tert-butyl methyl ether
i-PrOAc = iso-propyl acetate

TABLE 6

Influence of catalyst loading:[1]

| Entry | Substrate/catalyst ratio | LC-MS yield/%[2] | ee (sense)/%[3] |
|---|---|---|---|
| 1 | 400 | 59 | 86 (S) |
| 2 | 1000 | 59 | 87 (S) |
| 3 | 2000 | 64 | 86 (S) |

[1]Reaction conditions: (NBD)$_2$RhBF$_4$; (S)-Phanephos; Ligand/Rh = 3; 200 mg 6-chloro-3-(phenyl-d$_5$)-inden-1-one (I); 3 mL EtOAc; hydrogen gas (4 bar); room temperature; 18 h.
[2]UV area percentage in LC-MS.
[3]From analysis of the reaction mixture by chiral HPLC.

Example 1

To a solid mixture of (NBD)$_2$RhBF$_4$ (0.8 mg, 2 µmol) and (S)-Phanephos (3.5 mg, 6.1 µmol) was added EtOAc (oxygen-free, 4.0 mL). The mixture was stirred vigorously for 30 min, after which a solution of 6-chloro-3-(phenyl-d$_5$)-inden-1-one (I) (1.00 g, 4.07 mmol) in EtOAc (oxygen-free, 3.0 mL) was added to the foggy solution. The resulting mixture was hydrogenated at 4 bar hydrogen gas with stirring for 18 h. Analysis by chiral HPLC of the reaction mixture showed the formation of (S)-6-chloro-3-(phenyl-d$_5$)-indan-1-one (IX) with 86% ee. The reaction mixture was evaporated to dryness in vacuo, and the residue was redissolved in minimum boiling ethanol, and the solution was allowed to cool slowly to room temperature. The formed precipitate was filtered from solution and dried in vacuo to yield (S)-6-chloro-3-(phenyl-d$_5$)-indan-1-one (IX) (712 mg, 71%) as an off-white powder, with 98% ee according to chiral HPLC analysis. A second crop could be obtained by cooling the filtrate in the freezer (−5° C.) to obtain (S)-6-chloro-3-(phenyl-d$_5$)-indan-1-one (IX) (64 mg, 6%), with 93% ee according to chiral HPLC analysis.

Analytical data (NMR and LC-MS) for compound (IX) were the same as those reported above for compound (VIII).

Example 2

To a solid mixture of [(S)-Phanephos][NBD]RhBF$_4$ complex (17 mg, 20 µmol) and 6-chloro-3-(phenyl-d$_5$)-inden-1-one (I) (10.0 g, 40.7 mmol) was added EtOAc (oxygen-free, 100 mL). The mixture was hydrogenated at 4 bar hydrogen gas with stirring for 2 h. Analysis by chiral HPLC of the reaction mixture showed the formation of (S)-6-chloro-3-(phenyl-d$_5$)-indan-1-one (IX) with 89% ee. The reaction mixture was stirred with activated charcoal (1 g) for 1 h, and filtered through Celite. The filtrate was evaporated to dryness in vacuo, and the residue was redissolved in minimum boiling ethanol, and the solution was allowed to cool slowly to room temperature. The formed precipitate was filtered from solution and dried in vacuo to yield (S)-6-chloro-3-(phenyl-d$_5$)-indan-1-one (IX) (7.1 g, 70%), with 99% ee according to chiral HPLC analysis.

Analytical data (NMR and LC-MS) for compound (IX) were the same as those reported above for compound (VIII).

Example 3

To a solid mixture of (NBD)$_2$RhBF$_4$ (435 mg, 1.16 mmol) and (S)-Phanephos (1.31 g, 2.27 mmol) was added EtOAc (oxygen-free, 300 mL). The mixture was stirred vigorously for 30 min, and added to a suspension of 6-chloro-3-(phenyl-d$_5$)-inden-1-one (I) (400 g, 1.63 mol) in EtOAc (oxygen-free, 2.7 L). The mixture was transferred to a 25 L autoclave and hydrogenated at 4 bar hydrogen gas for 22 h at rt. The reaction mixture was then mixed with activated charcoal (56 g) and stirred for 1 h, and filtered through Arbocel BC 200® using additional EtOAc (200 mL). The filtrate was evaporated to dryness in vacuo, and ethanol (1.2 L) was added. The mixture was heated to 80° C. to form a homogeneous solution, that was subsequently allowed to cool slowly with stirring to rt, and the resulting suspension was further cooled in an ice-water bath, and filtered. The precipitate was washed with ice-chilled ethanol (200 mL), and dried in vacuo at 50° C. for one day to yield (S)-6-chloro-3-(phenyl-d$_5$)-indan-1-one (IX) (339 g, 84%) as a solid, with 99% ee according to chiral HPLC analysis and a purity of >99% according to LC-MS analysis.

Analytical data (NMR and LC-MS) for compound (IX) were the same as those reported above for compound (VIII).

F. Synthesis of (±)-cis-6-chloro-3-(phenyl-d$_5$)-indan-1-ol (X)

Scheme 10:

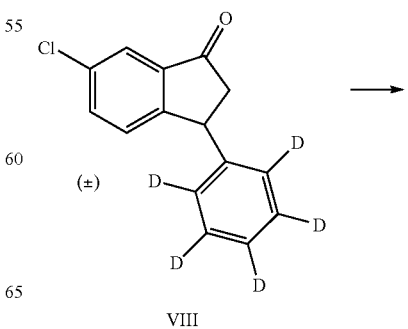

VIII

-continued

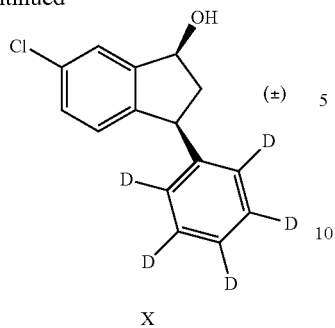

X

To a suspension of sodium borohydride (443 mg, 11.7 mmol) in IPA (10.0 mL) was added a solution of (±)-6-chloro-3-(phenyl-d$_5$)-indan-1-one (VIII) (1.45 g, 5.85 mmol) in IPA (10.0 mL) and THF (5.0 mL) at −10° C. The mixture was allowed to warm to rt slowly overnight. Aq. HCl-solution (10 mL, 4 M) was added carefully while the reaction mixture was cooled in an ice-water bath to keep the temperature at or below room temperature. The resulting mixture was concentrated by evaporation in vacuo, and water (20 mL) was added. The aqueous mixture was extracted with EtOAc three times (3×30 mL). The combined extracts were washed with brine (20 mL), dried over MgSO$_4$, and filtered. The filtrate was co-evaporated with silica gel. The obtained material was loaded onto a silica gel column and elution with heptane-EtOAc (4:1) afforded (±)-cis-6-chloro-3-(phenyl-d$_5$)-indan-1-ol (X) (1.43 g, 98%) as an off-white solid, with a cis:trans ratio of 97:3 according to $^1$H NMR analysis, and purity of 97% according to LC-MS analysis.

Analytical data for (±)-cis-6-chloro-3-(phenyl-d$_5$)-indan-1-ol (X):

$^1$H NMR (600 MHz, CDCl$_3$) δ$_H$ 1.96 (ddd, J=8.0, 13.0 Hz, 1H), 2.06 (d, J=8.0 Hz, 1H), 3.03 (dt, J=8.0, 13.0 Hz, 1H), 4.14 (t, J=8.0 Hz, 1H), 5.25 (q, J=8.0 Hz, 1H), 6.86 (dd, J=1.0, 8.0 Hz, 1H), 7.20 (dd, J=2.0, 8.0 Hz, 1H), 7.45 (d, J=2.0 Hz, 1H); $^{13}$C NMR (150 MHz, CDCl$_3$) δ$_C$ 47.3, 47.8, 74.7, 124.1, 126.3, 126.4, 128.0, 128.5, 129.3, 133.2, 143.6, 144.1, 147.2; LC-MS (APPI): m/e calc. for C$_{15}$H$_9$D$_5$ClO [M+H]$^+$ 250.1. found 250.0.

G. Synthesis of (±)-trans-1-(6-chloro-3-(phenyl-d$_5$)-indan-1-yl)-3,3-dimethyl-piperazine maleate (XII) via (±)-cis-3,5-Dichloro-1-(phenyl-d$_5$)-indan (XI)

Scheme 11:

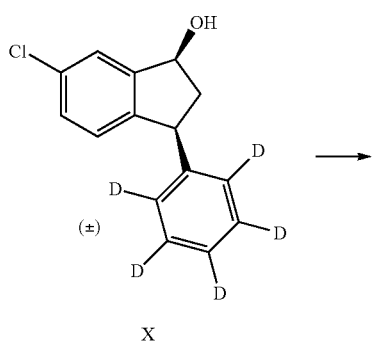

X

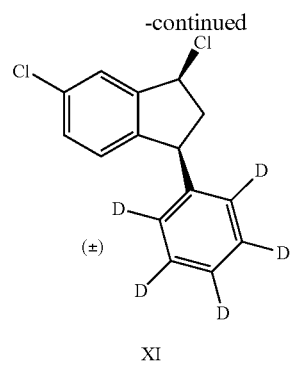

XI

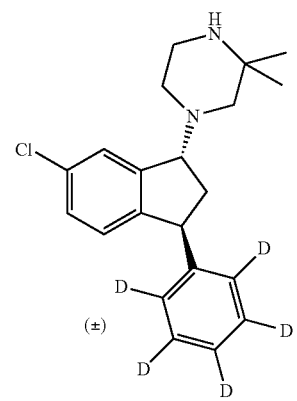

XII: Racemate, 1:1 maleate salt

Thionyl chloride (2.01 kg, 16.9 mol) and THF (7.2 kg) were mixed and the mixture was cooled to 10-15° C. A solution of (±)-cis-6-chloro-3-(phenyl-d$_5$)-indan-1-ol (X) (2.76 kg, 11.1 mol) in THF (7.2 kg) was slowly added and after completion THF (5.9 kg) was added. The reaction mixture was stirred at 15° C. for approximately 90 h. Water (16.7 kg) was cooled to 11° C. and added slowly to the reaction mixture, afterwards aq. NaOH-solution (7.8 kg, 27.7% w/w) was added slowly, followed by EtOAc (10 kg). The mixture was stirred for 20-40 min. The phases were separated and the organic phase was reduced to a volume of approximately 6 L by distillation. MIBK (16 kg) was added and the volume was reduced to approximately 8 L by distillation to yield a solution of compound (XI). Potassium carbonate (1.58 kg, 11.4 mol), 2,2-dimethylpiperazine (1.69 kg, 14.8 mol) and MIBK (13.6 kg) were added. The reaction mixture was stirred 35 h at 90-95° C. After cooling to room temperature water (11 kg) was added and the mixture was stirred for 30-60 min. The phases were separated. Water (13.7 kg) was added to the organic phase and the mixture was stirred slowly for 30-60 min. The phases were separated and the organic phase was blank filtered. MIBK (5 kg), water (7.8 kg) and aq. HCl-solution (5.9 kg, 36% w/w) were added and the mixture was stirred at 50° C. for 30 to 60 min. The phases were separated, and MIBK (8 kg) was added to the water phase and the mixture was cooled to 10-15° C. A mixture of MIBK (3.5 kg) and aq. NH$_3$-solution (7.8 kg, 25% w/w) were slowly added to the mixture and the reaction mixture was stirred at 20-25° C. for 60-90 min. The phases were separated and the organic phase was washed with water (10.5 kg). The organic phase was reduced to 8 L by distillation. Maleic acid (1.19 kg, 10.3 mol) and MIBK (9 kg) was added and the reaction mixture was afterwards warmed to 75-80° C. After cooling to 10-15° C. the precipitate was filtered off and washed with MIBK (10 kg). The solid was dried in a vacuum oven at 50° C. for approximately 20 h to give (±)-trans-1-(6-chloro-3-(phenyl-$d_5$)-indan-1-yl)-3,3-dimethyl-piperazine maleate (XII) (3.47 kg, 68%).

Analytical data for (±)-trans-1-(6-chloro-3-(phenyl-$d_5$)-indan-1-yl)-3,3-dimethyl-piperazine maleate (XII):
$^1$H NMR (250 MHz, DMSO-$d_6$) $\delta_H$ 1.31 (s, 3H), 1.33 (s, 3H), 2.12 (ddd, J=6.0, 8.0, 14.0 Hz, 1H), 2.31 (d, J=12.0 Hz, 1H), 2.58-2.50 (m, 3H), 2.77 (bs, 1H), 3.16 (bs, 2H), 3.37 (bs, 1H), 4.48 (dd, J=6.0, 8.5 Hz, 1H), 4.56 (dd, J=5.0, 8.0 Hz, 1H), 6.04 (s, 2H, maleic acid), 6.98 (d, J=8.0 Hz, 1H), 7.29 (dd, J=2.0, 8.0 Hz, 1H), 7.39 (d, J=1.5 Hz, 1H), 8.60 (bs, 2H).

H. Synthesis of (±)-trans-1-(6-chloro-3-(phenyl-$d_5$)-indan-1-yl)-1($d_3$),2,2-trimethyl-piperazine succinate (XIII)

Scheme 12:

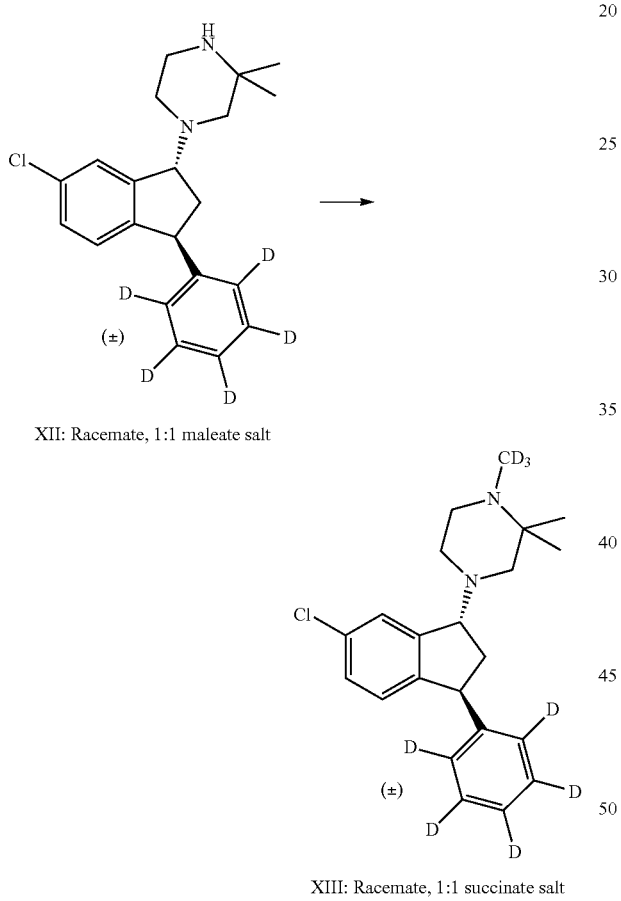

XII: Racemate, 1:1 maleate salt

XIII: Racemate, 1:1 succinate salt

Compound (XII) (1.1 kg, 2.38 mol), TBME (11 L), water (1.8 L) and aq. NH$_3$-solution (1 L, 25% w/w) were stirred for 1-2 h. The phases were separated and the organic phase was washed with water (2×2 L). An aq. KOH-solution (254 g, 3.85 mol, 85% w/w) and water (1.5 L) were added to the organic phase, followed by the addition of methyliodide-$d_3$ (450 g, 3.11 mol). The reaction mixture was stirred at 20-25° C. for 16-24 h. Water (2 L) was added and the precipitating byproduct was filtered off. Water (0.8 L) and aq. NH$_3$-solution (0.2 L, 25% w/w) were added to the filtrate and the mixture was stirred for 20-40 min. The phases were separated and the organic phase was washed with water (2 L). The phases were separated and acetylchloride (38 g, 0.48 mol) was added to the organic phase which was stirred for 20-40 min. Water (0.8 L) and an aq. NH$_3$-solution (0.2 L, 25% w/w) were added and the mixture was stirred for 20-40 min. The phases were separated and the organic phase was washed with water (2 L). The organic phase was evaporated to dryness. Succinic acid (225 g, 1.91 mol) and acetone were added as to reach a total reaction volume of 6-6.5 L. The reaction mixture was warmed to reflux and afterwards cooled to 5-10° C. The precipitate was filtered off and washed with acetone (1 L). The solid was dried in a vacuum oven at 50° C. for more than 16 h to give compound (XIII) (630 g, 55%).

Analytical data for (±)-trans-1-(6-chloro-3-(phenyl-$d_5$)-indan-1-yl)-1($d_3$),2,2-trimethyl-piperazine succinate (XIII):
$^1$H NMR (600 MHz, DMSO-$d_6$) $\delta_H$ 1.02 (s, 3H), 1.04 (s, 3H), 2.02 (ddd, J=6.0, 8.0, 14.0 Hz, 1H), 2.13 (d, J=11.0 Hz, 1H), 2.31 (bs, 1H), 2.37 (s, 4H, succinic acid), 2.46-2.41 (m, 1H), 2.65-2.56 (m, 4H), 4.46 (dd, J=6.0, 9.0 Hz, 1H), 4.46 (dd, J=5.0, 8.0 Hz, 1H), 6.95 (d, J=8.0 Hz, 1H), 7.26 (dd, J=2.0, 8.0 Hz, 1H), 7.33 (d, J=2.0 Hz, 1H).

I. Synthesis of 4-((1R,3S)-6-chloro-3-(phenyl-$d_5$)-indan-1-yl)-1($d_3$),2,2-trimethyl-piperazine L-(+)-tartrate (XIV) by resolution Scheme 13:

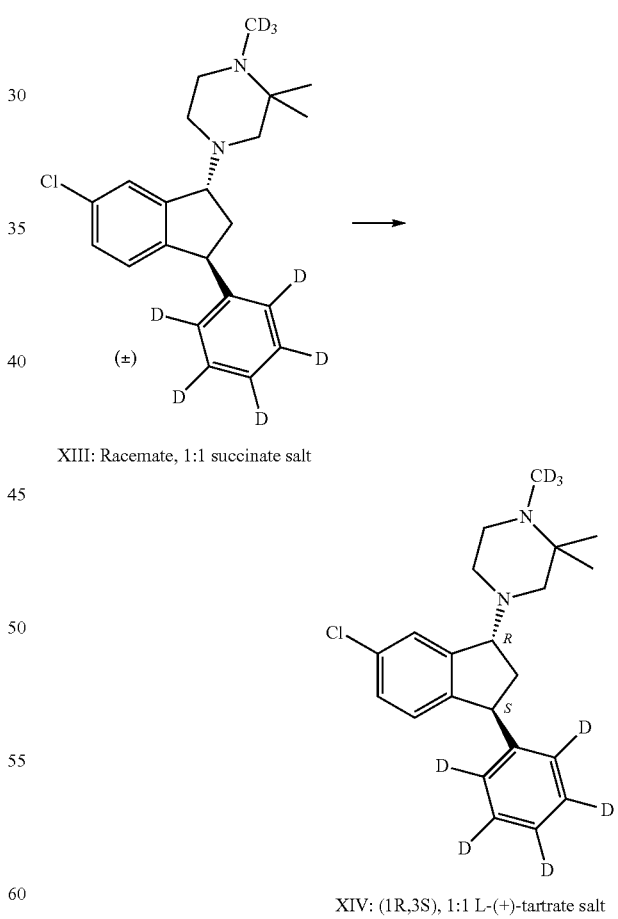

XIII: Racemate, 1:1 succinate salt

XIV: (1R,3S), 1:1 L-(+)-tartrate salt

Compound (XIII) (1.00 kg, 2.08 mol), EtOAc (8 L), water (2 L) and aq. NH$_3$-solution (1 L, 25% w/w) were stirred for 0.5-1 h. The phases were separated and the organic phase was washed with water (2 L). The organic phase was reduced to approximately 1.5 L by distillation. Acetone (10 L) and L-(+)- tartaric acid (312 g, 2.08 mol) were added. The mixture was warmed to reflux and afterwards cooled to 5-10° C. The precipitate was filtered off, and washed with acetone (1.2 L). The wet filtercake was mixed with ethanol (11 L). The mixture was warmed to reflux and afterwards cooled to 5-10° C. The precipitate was filtered off and washed with absolute ethanol (1.2 L). The solid was dried in a vacuum oven at 50° C. for more than 16 h to give compound (XIV) (395 g, 37% yield).

Analytical data for 4-((1R,3S)-6-chloro-3-(phenyl-$d_5$)-indan-1-yl)-1($d_3$),2,2-trimethyl-piperazine L-(+)-tartrate (XIV):

$^1$H NMR (600 MHz, DMSO-$d_6$) $\delta_H$ 1.18 (s, 3H), 1.21 (s, 3H), 2.04 (ddd, J=6.0, 8.0, 14.0 Hz, 1H), 2.31 (d, J=12.0 Hz, 1H), 2.61-2.50 (m, 3H), 2.77 (bs, 1H), 2.95 (bs, 1H), 4.07 (s, 2H, tartrate), 4.45 (dd, J=6.0, 8.5 Hz, 1H), 4.50 (dd, J=5.0, 8.0 Hz, 1H), 6.96 (d, J=8.0 Hz, 1H), 7.27 (d, J=8.0 Hz, 1H), 7.36 (s, 1H).

J. Synthesis of (1S,3S)-6-chloro-3-(phenyl-$d_5$)-indan-1-ol (Xa)

Scheme 14:

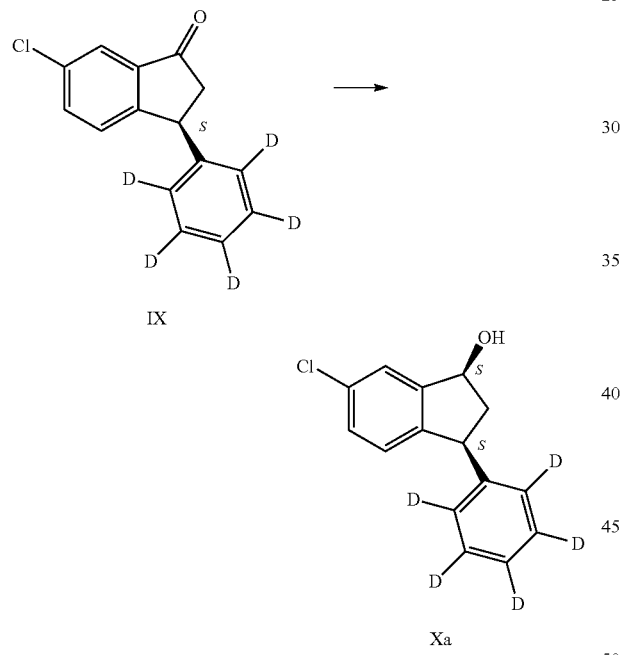

Sodium borohydride (67 g, 1.77 mol) was dissolved in IPA (2.1 L) and the solution was cooled to −10° C. (S)-6-chloro-3-(phenyl-$d_5$)-indan-1-one (IX) (438 g, 1.77 mol) was dissolved in THF (2.3 L) and IPA (0.4 L). The solution of (S)-6-chloro-3-(phenyl-$d_5$)-indan-1-one (IX) was added to the sodium borohydride solution over a period of 2 h 24 min with a maximum temperature of −4° C. during the addition. The reaction was stirred overnight while the temperature reached room temperature. The reaction was cooled to −2° C. and aq. HCl-solution (1.55 L, 4 M) was added over a period of 1 h 35 min. The volume of the reaction was reduced by distillation in vacuo to approximately 2.5 L. Water (2.5 L) and toluene (4 L) was added and the reaction was stirred at 45° C. for 15 min. The phases were separated and the organic phase was washed with aq. NaCl-solution (3 L, 5% w/w). The phases were separated and the organic phase reduced by distillation in vacuo (max. 70° C.) to approximately 1.4 L. The organic phase was added over a period of 9 min to heptane (12.5 L). The reaction was cooled to −5° C. and the formed precipitate was filtered off 1 h 20 min later. The precipitate was washed with heptane (1 L) and then dried in a vacuum oven at 40° C. overnight to yield (1S,3S)-6-chloro-3-(phenyl-$d_5$)-indan-1-ol (Xa) (377 g, 86%) as an off-white solid, with a purity of 99.5% according to HPLC analysis (method 2).

Analytical data (NMR and LC-MS) for compound (Xa) were the same as those reported above for compound (X).

K. Synthesis of 4-((1R,3S)-6-chloro-3-(phenyl-$d_5$)-indan-1-yl)-1($d_3$),2,2-trimethyl-piperazine L-(+)-tartrate (XIV) via (1S,3S)-3,5-Dichloro-1-(phenyl-$d_5$)-indan (XIa)

Scheme 15:

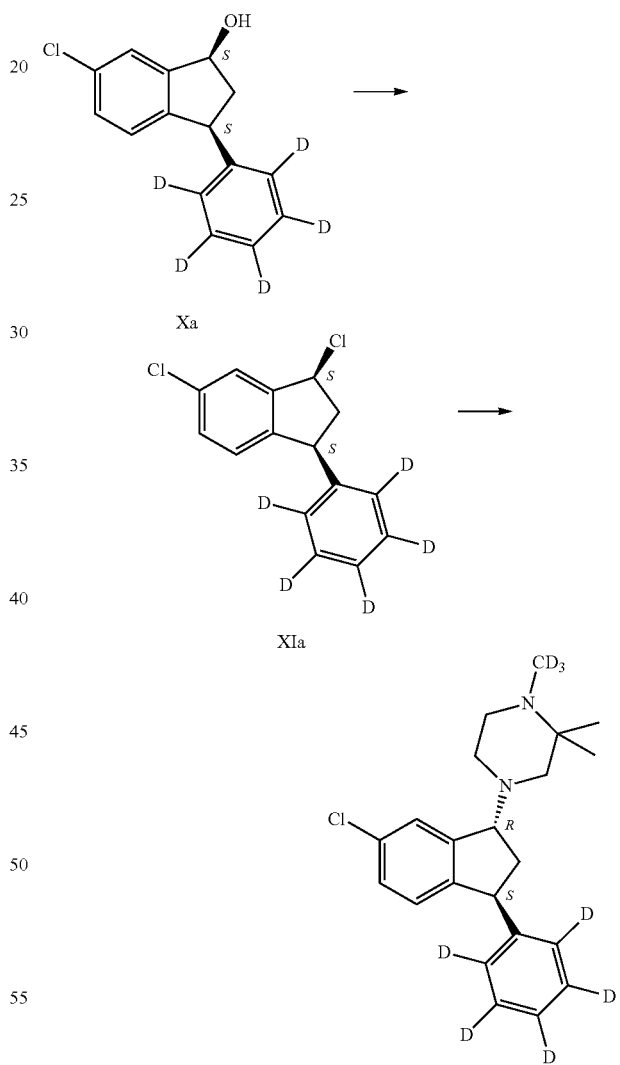

XIV: (1R,3S), 1:1 L-(+)-tartrate salt

An ice-cold solution of compound (Xa) (25 g, 100 mmol) in 2-MeTHF (80 mL) was added to an ice-cold solution of thionylchloride (11.0 mL, 152 mmol) in 2-MeTHF (60 mL) over a period of 10 min, with a maximum temperature of 1° C. The reaction was stirred overnight at room temperature, then cooled to 2° C., before water (180 mL) was added over a period of 25 min, keeping the temperature below 18° C. The pH was adjusted to 7 by addition of aq. NH$_3$-solution (34 mL, 25% w/w) and afterwards the phases were separated. The organic phase was evaporated in vacuo and the resulting oil stripped once with MIBK (50 mL) to yield crude compound (XIa). MIBK (160 mL), potassium carbonate (42.8 g, 310 mmol) and compound (XVI) (43.1 g, 120 mmol) were added and the reaction was heated at 90° C. for 24 h. The reaction was cooled to room temperature and then water (300 mL) was added. The reaction was stirred for 15 min, the phases were separated and the organic phase washed with water (300 mL). The phases were separated and acetyl chloride (1.0 ml) was added to the organic phase. The reaction was stirred for 3 h, then water (20 mL) and aq. NH$_3$-solution (6 mL, 25% w/w) were added. The phases were separated and the organic phase washed with water (130 mL). The organic phase was filtered through Arbocel BC-200 and then aq. HCl-solution (240 mL, 1.08 mol, 4.5 M) were added. The reaction was warmed to 50° C., the phases were separated and to the water phase were added MIBK (300 mL) and then aq. NH$_3$-solution (180 mL, 25% w/w). The phases were separated and the organic phase washed with water (300 mL) and afterwards reduced in volume by evaporation in vacuo. The resulting oil was stripped with acetone (100 mL). The oil was then dissolved in ethanol (300 mL) and L-(+)-tartaric acid (15.0 g, 100 mmol) was added. The reaction was warmed to reflux and then cooled to room temperature. The resulting precipitate was filtered off and the solid was washed with acetone (50 mL). The solid was dried in a vacuum oven at 50° C. overnight to yield compound (XIV) (29.8 g, 58%), with a purity of 97.8% according to HPLC analysis (method 3).

Analytical data (NMR and LC-MS) for compound (XIV) were the same as those reported above.

L. Synthesis of 4-((1R,3S)-6-chloro-3-(phenyl-d$_5$)-indan-1-yl)-1(d$_3$),2,2-trimethyl-piperazine fumarate (XV) via (1S,3S)-3,5-Dichloro-1-(phenyl-d$_5$)-indan (XIa)

Scheme 16:

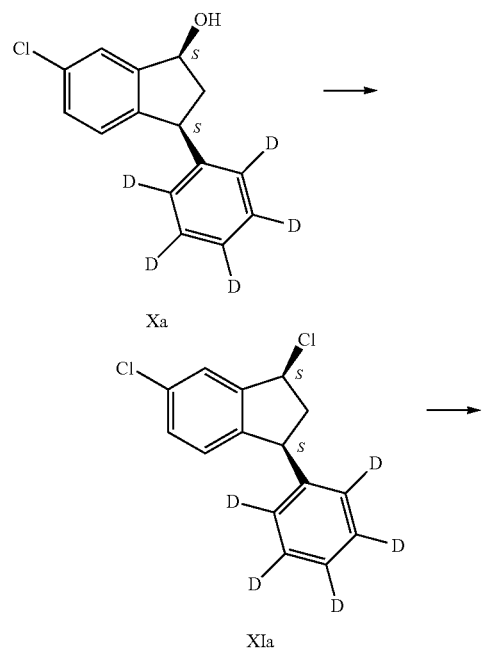

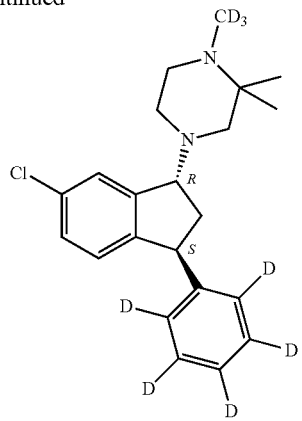

XV: (1R,3S), 1:1 fumarate salt

An ice-cold solution of compound (Xa) (23.7 g, 94.9 mmol) in 2-MeTHF (80 mL) was added to an ice-cold solution of thionylchloride (10.3 mL, 142 mmol) in 2-MeTHF (60 mL) over a period of 10 min, with a maximum temperature of 1° C. The reaction was stirred overnight at room temperature, then cooled to 3° C., before water (180 mL) was added over a period of 25 min, keeping the temperature below 16° C. The pH was adjusted to 7 by addition of aq. NH$_3$-solution (35 mL, 25% w/w) and afterwards the phases were separated. The organic phase was evaporated in vacuo and the resulting oil stripped once with MIBK (50 mL) to yield crude compound (XIa). MIBK (160 mL), potassium carbonate (40.7 g, 295 mmol) and compound (XVI) (40.9 g, 114 mmol) were added and the reaction was heated at 80° C. for 68 h. The reaction was cooled to 39° C. and then water (270 mL) was added. The reaction was stirred for 15 min, the phases were separated and the organic phase washed with water (270 mL). The phases were separated and acetyl chloride (0.9 ml) was added to the organic phase. The reaction was stirred for 72 h, then water (25 mL) and aq. NH$_3$-solution (7 mL, 25% w/w) were added. The phases were separated and the organic phase washed with aq. NaCl-solution (100 mL, 7.5% w/w) and subsequently with water (100 mL). The organic phase was filtered through Arbocel BC-200 and then aq. HCl-solution (250 mL, 1.0 mol, 4.0 M) was added. The reaction was warmed to 55° C., the phases were separated and to the water phase were added MIBK (300 mL) and then aq. NH$_3$-solution (100 mL, 25% w/w). The phases were separated and the organic phase washed with water (300 mL) and afterwards reduced in volume by evaporation in vacuo. The resulting oil was stripped with acetone (200 mL) and then with ethanol (200 mL). The oil was then dissolved in ethanol (200 mL) and fumaric acid (9.75 g, 84.0 mmol) was added. The reaction was warmed to 55° C. and then cooled to room temperature. The resulting precipitate was filtered off and the solid washed with ethanol twice (2×25 mL). The solid was dried in a vacuum oven at 50° C. for two days to yield compound (XV) (26.4 g, 58%), with a purity of 99.2% according to HPLC analysis (method 3).

Analytical data for 4-((1R,3S)-6-chloro-3-(phenyl-d$_5$)-indan-1-yl)-1(d$_3$),2,2-trimethyl-piperazine fumarate (XV):

$^1$H NMR (250 MHz, CDCl$_3$) δ$_H$ 1.14 (s, 3H), 1.16 (s, 3H), 2.04 (ddd, J=6.0, 8.0, 13.5 Hz, 1H), 2.26 (d, J=12.0 Hz, 1H), 2.73-2.40 (m, 3H), 2.86-2.75 (m, 1H), 2.92-2.86 (m, 2H), 4.52-4.41 (m, 2H), 6.53 (s, 2H, fumarate), 6.95 (d, J=8.0 Hz, 1H), 7.26 (dd, J=2.5, 8.0 Hz, 1H), 7.34 (d, J=2.5 Hz, 1H).

M. Synthesis of tert-butyl 3,3-dimethylpiperazine-1-carboxylate hemi-D,L-tartrate (XVIII)

Scheme 17:

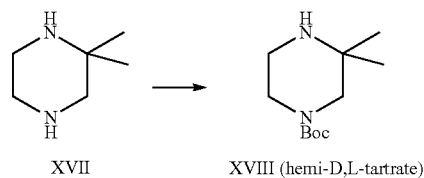

XVII → XVIII (hemi-D,L-tartrate)

2,2-dimethylpiperazine (11.5 kg, 101 mol) was dissolved in ethanol (48.5 L) and the solution was cooled to approximately 9° C. Di-tert-butyl dicarbonate (21.9 kg, 100 mol) was dissolved in ethanol (41.7 L). The solution of di-tertbutyl dicarbonate was added to the solution of dimethylpiperazine over a period of 2 h 30 min, keeping the temperature of the reaction below 15° C. Ethanol (12.4 L) was added and the solution was stirred overnight at a temperature between 12-25° C. The reaction was warmed to reflux and 75 L were distilled off. Ethanol (76 L) was added to the reaction and the solution was heated to 52° C. and transferred to a suspension of D,L-tartaric acid (7.5 kg, 50.0 mol) in ethanol (25.2 L), and warmed to 51° C. Ethanol (25.3 L) was added and the reaction was kept at 20° C. overnight. The precipitate was filtered off and washed with ethanol (28.1 L). The solid was dried in a vacuum oven at 50° C. overnight to yield compound (XVIII) (27.1 kg, 93%) with 99% purity according to GC analysis.

Analytical data for tert-butyl 3,3-dimethylpiperazine-1-carboxylate hemi-D,L-tartrate (XVIII):

$^1$H NMR (250 MHz, CDCl$_3$) $\delta_H$ 1.35 (s, 6H), 1.46 (s, 9H), 3.10 (bs, 2H), 3.42 (bs, 2H), 3.63 (bs, 2H), 4.29 (s, 1H, tartrate), 7.60 ppm (bs, 3H); $^{13}$C NMR (62.5 MHz, CDCl$_3$) $\delta_C$ 22.3, 28.3, 39.0, 40.8, 50.2, 51.8, 53.6, 73.6 (tartrate), 80.6, 154.2, 178.3 (tartrate).

N. Synthesis of 1(d$_3$),2,2-trimethylpiperazine bis-2,2,2-trifluoroacetate (XVI)

Scheme 18:

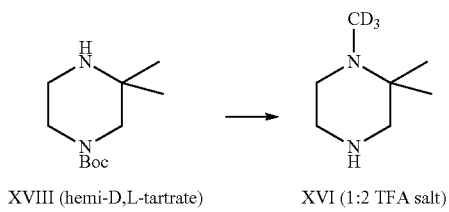

XVIII (hemi-D,L-tartrate) → XVI (1:2 TFA salt)

Compound XVIII (23.0 kg, 79.5 mol) was suspended in toluene (133 L), water (85.2 L) and aq. NaOH-solution (14.1 kg, 27.7% w/w) were added and the reaction was stirred for 1 h. After phase separation the organic phase was added to potassium carbonate (11.1 kg, 80.3 mol). N-methylpyrrolidine (7.0 kg) was added. Iodomethane-d$_3$ (12.7 kg, 87.6 mol) was dissolved in toluene (11.5 L) and then added to the reaction, followed by toluene (11.5 L). The reaction was stirred at 23° C. overnight. After an in-process control showed that 5.7% compound (XVIII) was left, iodomethane-d$_3$ (0.9 kg, 6.21 mol) and toluene (12.7 L) were added and the reaction was stirred overnight at 23° C. Water (85 L) and aq. NH$_3$-solution (3.5 kg, 25% w/w) were added and the reaction was stirred for 40 min. The phases were separated and the organic phase was reduced by distillation in vacuo to approximately 20 L. The reaction was cooled to 0° C. and trifluoroacetic acid (38.0 kg, 333 mol) was added over a period of 36 min. The reaction was stirred at 39° C. overnight and then cooled to 13° C. Diethyl ether (77.1 L) was added and the reaction was stirred at approximately 22° C. overnight. The reaction was cooled to 8° C., stirred there for 3.5 h and then filtered. The filtercake was washed with diethylether (44.9 L) and then with more diethylether (30.8 L). The resulting solid was dried in a vacuumoven at 50° C. overnight to yield compound (XVI) (23.4 kg, 82%) with a purity of 93.2% according to GC analysis.

Analytical data for 1(d$_3$),2,2-trimethylpiperazine bis-2,2,2-trifluoroacetate (XVI):

$^1$H NMR (250 MHz, D$_2$O) $\delta_H$ 1.35 (s, 6H), 3.16 (d, J=14.5 Hz, 1H), 3.31-3.21 (m, 1H), 3.58-3.35 ppm (m, 4H); $^{13}$C NMR (62.5 MHz, D$_2$O) $\delta_C$ 17.0, 23.8, 37.0, 41.9, 47.3, 51.7, 60.8, 117.6 (q, J=36 Hz, TFA), 164.0 (q, J=291 Hz, TFA).

The invention claimed is:

1. A compound having the structure (I)

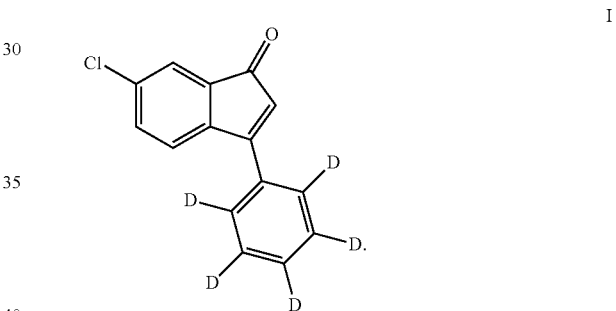

2. A process for production of compound (I), wherein compound (I) is obtained via reaction of 3-bromo-6-chloroinden-1-one with a phenyl-d$_5$ arylboronic acid or a phenyl-d$_5$ arylboronic ester.

3. The process according to claim 2 wherein the arylboronic acid or arylboronic ester is 4,4,5,5-tetramethyl-2-d$_5$-phenyl-[1,3,2]dioxaborolane.

4. The process of claim 2 comprising the following steps
   i. 2,2'-azo-bis-isobutyronitrile and N-bromosuccinimide is added to a solution comprising 6-chloro-1-indanone;
   ii. Triethylamine is added to the solution of step a) to obtain 3-bromo-6-chloro-inden-1-one; and
   iii. 3-bromo-6-chloro-inden-1-one is separated and reacted with 4,4,5,5-tetramethyl-2-d$_5$-phenyl-[1,3,2]dioxaborolane in the presence of an appropriate catalyst and base to obtain compound (I).

5. The process of claim 4 wherein step iii is carried out in the presence of palladium acetate and triphenylphosphine.

6. The process according to claim 2 comprising the steps of
   1. Synthesis of 6-chloro-3-(phenyl-d$_5$)-1H-indene (IV) by reaction between an organometallic species obtained from monohalogenated benzene-d$_5$ and 5-chloro-1-indanone (V) followed by dehydration; and
   2. Reaction of 6-chloro-3-(phenyl-d$_5$)-1H-indene (IV) to compound (XIX) and further oxidative cleavage thereof to obtain compound (I).

7. The process according to claim 6 comprising the steps of
   i. Synthesis of 6-chloro-3-(phenyl-d$_5$)-1H-indene (IV) by Grignard reaction between bromobenzene-d$_5$, magnesium and 5-chloro-1-indanone followed by dehydration; and
   ii. Reacting 6-chloro-3-(phenyl-d$_5$)-1H-indene of step i) with 1,1-dimethoxy-N,N-dimethylmethanamine of the formed enamine intermediate (XIX) followed by oxidative cleavage to obtain compound (I).

8. The process of claim 6 wherein the oxidative cleavage in step b is carried out by use of an oxidative agent selected from the group consisting of sodium metaperiodate, potassium metaperiodate, ozone, potassium dichromate, sodium dichromate, singlet oxygen and m-chloroperbenzoic acid.

9. A process comprising the steps
   i. Compound (I) of claim 1 is reduced to obtain 6-chloro-3-(phenyl-d$_5$)-1H-inden-1-ol (VIa); and
   ii. Compound (VIa) is converted to 6-chloro-3-(phenyl-d$_5$)-indan-1-one (VIIIa) via base-induced rearrangement.

10. A process comprising the steps
    i. Compound (I) of claim 1 is converted to (S)-6-chloro-3-(phenyl-d$_5$)-1H-inden-1-ol (VII) via enantioselective reduction in the presence of enantioselective catalyst and reductant; and
    ii. Compound (VII) is converted to (S)-6-chloro-3-(phenyl-d$_5$)-indan-1-one (IX) via base-induced rearrangement.

11. A process comprising conversion of Compound (I) of claim 1 to obtain 6-chloro-3-(phenyl-d$_5$)-indan-1-one (VIIIa) via hydrogenation in the presence of a suitable catalyst in a suitable solvent.

12. A process comprising conversion of Compound (I) of claim 1 to obtain (S)-6-chloro-3-(phenyl-d$_5$)-indan-1-one (IX) via asymmetric hydrogenation in the presence of a suitable catalyst, a chiral phosphine ligand and a suitable solvent.

13. A process wherein the compounds obtained in claim 9 are converted to 3,5-dichloro-1-(phenyl-d$_5$)-indan, the process comprising the following steps
    i. Reduction of (±)-6-chloro-3-(phenyl-d5)-indan-1-one (VIII), 6-chloro-3-(phenyl-d5)-indan-1-one (VIIIa) or (S)-6-chloro-3-(phenyl-d5)-indan-1-one (IX) to obtain the corresponding indanol:
       (±)-cis-6-chloro-3-(phenyl-d5)-indan-1-ol (X), 6-chloro-3-(phenyl-d5)-indan-1-ol (Xb) or (1S,3S)-6-chloro-3-(phenyl-d5)-indan-1-ol (Xa) in the presence of a suitable reduction agent; and
    ii. Chlorination, of any of the compounds obtained in step i to obtain the corresponding chlorinated indan compound (±)-cis-3,5-dichloro-1-(phenyl-d5)-indan (XI), 3,5-dichloro-1-(phenyl-d5)-indan (XIb) or (1S,3S)-3,5-dichloro-1-(phenyl-d5)-indan (XIa).

14. A process wherein the (±)-cis-3,5-dichloro-1-(phenyl-d5)-indan (XI), 3,5-dichloro-1-(phenyl-d5)-indan (XIb) or (1S,3S)-3,5-dichloro-1-(phenyl-d5)-indan (XIa) as obtained in claim 13 are converted to a pharmaceutically acceptable salt of (±)-trans-1-(6-chloro-3-(phenyl-d$_5$)-indan-1-yl)-3,3-dimethyl-piperazine, 1-(6-chloro-3-(phenyl-d$_5$)-indan-1-yl)-3,3-dimethyl-piperazine or 1-((1R,3S)-6-chloro-3-(phenyl-d$_5$)-indan-1-yl)-3,3-dimethyl-piperazine, the process comprising the following steps
    i. reaction with 2,2-dimethylpiperazine or a compound that subsequently can be transformed to the 3,3-dimethylpiperazine moiety of (±)-trans-1-(6-chloro-3-(phenyl-d$_5$)-indan-1-yl)-3,3-dimethyl-piperazine, 1-(6-chloro-3-(phenyl-d$_5$)-indan-1-yl)-3,3-dimethyl-piperazine or 1-((1R,3S)-6-chloro-3-(phenyl-d$_5$)-indan-1-yl)-3,3-dimethyl-piperazine; and
    ii. formation and optionally precipitation of the pharmaceutically acceptable salt by addition of the corresponding acid.

15. A process wherein the pharmaceutically acceptable salt of (±)-trans-1-(6-chloro-3-(phenyl-d$_5$)-indan-1-yl)-3,3-dimethyl-piperazine, 1-(6-chloro-3-(phenyl-d$_5$)-indan-1-yl)-3,3-dimethyl-piperazine or 1-((1R,3S)-6-chloro-3-(phenyl-d$_5$)-indan-1-yl)-3,3-dimethyl-piperazine obtained in claim 14 is converted to a pharmaceutically acceptable salt of 4-((1R,3S)-6-chloro-3-(phenyl-d$_5$)-indan-1-yl)-1(d$_3$),2,2-trimethyl-piperazine, the process comprising the following steps
    i. alkylation in the presence of an active methyl-d$_3$ donor and a base; and
    ii. formation and optionally precipitation of the pharmaceutically acceptable salt by addition of the corresponding acid.

16. A process wherein the 3,5-dichloro-1-(phenyl-d$_5$)-indan obtained in claim 13 is converted to a pharmaceutically acceptable salt of 4-((1R,3S)-6-chloro-3-(phenyl-d$_5$)-indan-1-yl)-1(d$_3$),2,2-trimethyl-piperazine, the process comprising the following steps
    i. nucleophile substitution of 3,5-dichloro-1-(phenyl-d$_5$)-indan with 1(d$_3$),2,2-trimethylpiperazine bis-2,2,2-trifluoroacetate or a compound that subsequently can be transformed to the 1(d$_3$),2,2-trimethyl-piperazine moiety of 4-((1R,3S)-6-chloro-3-(phenyl-d$_5$)-indan-1-yl)-1(d$_3$),2,2-trimethyl-piperazine; and
    ii. formation and optionally precipitation of the pharmaceutically acceptable salt by addition of the corresponding acid.

* * * * *